US008236920B2

(12) United States Patent
Hida et al.

(10) Patent No.: US 8,236,920 B2
(45) Date of Patent: Aug. 7, 2012

(54) POLYARYLENE AND PROCESS FOR PRODUCING THE SAME

(75) Inventors: Noriyuki Hida, Sakai (JP); Seiji Oda, Ibaraki (JP); Takashi Kamikawa, Nara (JP); Katsuhiro Suenobu, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 639 days.

(21) Appl. No.: 12/224,672

(22) PCT Filed: Sep. 6, 2006

(86) PCT No.: PCT/JP2006/318092
§ 371 (c)(1),
(2), (4) Date: Sep. 3, 2008

(87) PCT Pub. No.: WO2007/102235
PCT Pub. Date: Sep. 13, 2007

(65) Prior Publication Data
US 2009/0036632 A1 Feb. 5, 2009

(30) Foreign Application Priority Data

Mar. 7, 2006 (JP) ................. 2006-060734

(51) Int. Cl.
*C08G 75/20* (2006.01)
*C08G 75/23* (2006.01)
*C08G 8/02* (2006.01)
*C07C 317/16* (2006.01)

(52) U.S. Cl. .......... 528/171; 528/86; 528/172; 528/391; 568/18; 568/34; 568/35

(58) Field of Classification Search .......... 528/86, 528/171, 172, 391; 568/18, 34, 35
See application file for complete search history.

(56) References Cited

U.S. PATENT DOCUMENTS

| 3,376,235 A | 4/1968 | Hartle |
| 2005/0159562 A1 | 7/2005 | Hayashi et al. |
| 2005/0239994 A1 | 10/2005 | Litt et al. |
| 2008/0004360 A1 | 1/2008 | Yamada et al. |

FOREIGN PATENT DOCUMENTS

| BE | 615 985 A1 | 7/1962 |
| EP | 1 721 922 A1 | 11/2006 |
| EP | 1 857 482 A1 | 11/2007 |
| JP | 2003-238665 | 8/2003 |
| JP | 2003 238665 A | 8/2003 |
| JP | 2003-238665 A | 8/2003 |
| JP | 2005-232439 | 9/2005 |
| JP | 2005 232439 A | 9/2005 |
| JP | 2005-248143 | 9/2005 |
| JP | 2005 248143 A | 9/2005 |
| JP | 2005-276642 | 10/2005 |
| JP | 2005-276642 A | 10/2005 |
| JP | 2005-314452 | 11/2005 |
| JP | 2005-314452 A | 11/2005 |
| JP | 2005-320523 | 11/2005 |
| JP | 2006-137792 | 6/2006 |
| JP | 2006-137792 A | 6/2006 |
| WO | WO 2006/095919 A1 | 9/2006 |

OTHER PUBLICATIONS

Granados-Focil, Sergio et al., "Novel Highly Conductive Poly(phenylene sulfonic acids) and its Evaluation as Proton Exchange Membranes for Fuel Cells", Polymeric Materials; Science & Engineering, 2003, 89, pp. 438,439.
Rulkens, Rudy, et al., "Rigid-rod polyelectrolytes: synthesis of sulfonated poly(p-phenylene)s", Macromol. Rapid Commun., 1994, 15, pp. 669-676.
Supplemental European Search Report filed in the corresponding application: EP 06797884, dated May 31, 2010.
Courtot, et al., "Contribution a l'etude de la serie du diphenyle// Biphenyl series", *Bulletin de la Societe Chimique de France*, vol. 49, 1931, pp. 1047-1065.
Irvin, et al., "Synthesis and Characterization of Chiral Conjugated Polymers of Optical Waveguides", *Trends in Optics and Photonics Series, Optical Society of America*, vol. 64, 2002, pp. 88-92.
Li, et al., "Substituent Effect to Prevent Autoxidation and Improve Spectral Stability in Blue Light-Emitting Polyfluorenes", *Chemistry—A European Journal*, vol. 11, No. 15, 2005, pp. 4450-4457.
Rulkens, et al., "Cylindrical Micelles of Wormlike Polyelectrolytes", *Langmuir*, vol. 15, 1999, pp. 4022-4025.
Rulkens, et al., "Rigid-rod polyelectrolytes: synthesis of sulfonated poly(p-phenylene)s", *Macromolecular Rapid Communications*, vol. 15, No. 9, 1994, pp. 669-676.
Rulkens, et al., "Rigid-rod Polyelectrolytes Based on Poly(p-Phenylene Sulfonic Acid)", Ber. Bunsenges. Phys. Chem., vol. 100, No. 6, 1996, ppl. 707-714.
Hassan, et al. "Aryl-Aryl Bond Formation One Century after the Discovery of the Ullmann Reaction", Chem. Rev., 2002, vol. 102, No. 5, pp. 1358 & 1379.
Office Action in JP Appln. No. 2006-245256 dated Aug. 31, 2011.
Vanhee, S. et al., "Synthesis and Characterization of Rigid Rod Poly(p-phenylenes)", Macromolecules, 1996, vol. 29, pp. 5136-5142.

*Primary Examiner* — Duc Truong
(74) *Attorney, Agent, or Firm* — Foley & Lardner LLP

(57) ABSTRACT

A dihalobiphenyl compound represented by the formula (1):

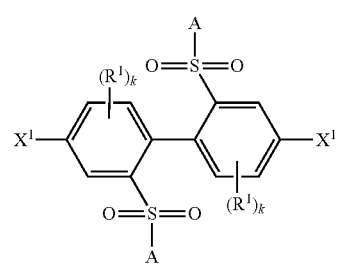

wherein A represents an amino group substituted with one or two C1-C20 hydrocarbon groups or a C1-C20 alkoxy group, $R^1$ represents a fluorine atom, a C1-C20 alkyl group, etc., $X^1$ represents a chlorine atom, a bromine atom or an iodine atom, an k represents an integer of 0 to 3, and
a polyarylene comprising a repeating unit represented by the formula (2):

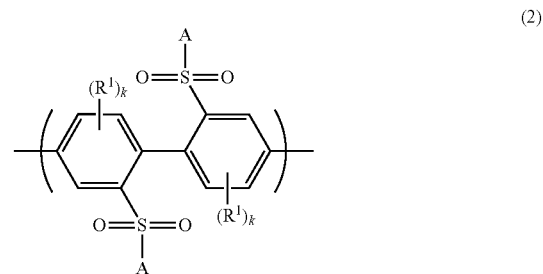

wherein A, $R^1$ and k represent the same meanings as defined above.

25 Claims, No Drawings

POLYARYLENE AND PROCESS FOR PRODUCING THE SAME

TECHNICAL FIELD

The present invention relates to a polyarylene and a process for producing the same.

BACKGROUND ART

A polyarylene having sulfonic acid groups is useful as a polyelectrolyte for proton-exchange membrane fuel cell. As a process for producing it, a process using a diphenyl dihalobiphenyldisulfonate as a monomer (e.g. Macromol. Rapid. Commun., 15, 669-676 (1994) and Polymeric Materials; Science & Engineering, 2003, 89, 438-439) has been known.

DISCLOSURE OF THE INVENTION

The present invention provides a dihalobiphenyl compound represented by the formula (1):

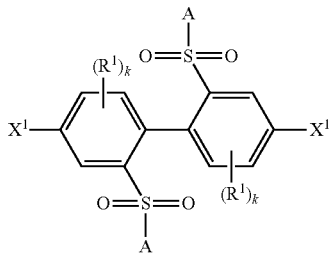

(1)

wherein A represents an amino group substituted with one or two C1-C20 hydrocarbon groups or a C1-C20 alkoxy group, and the above-mentioned hydrocarbon group and the alkoxy group may be substituted with at least one group selected from the group consisting of a fluorine atom, a C1-C20 alkoxy group, a C6-C20 aryl group, a C6-C20 aryloxy group, a C2-C20 acyl group and a cyano group,
$R^1$ represents a fluorine atom, a C1-C20 alkyl group, a C1-C20 alkoxy group, a C6-C20 aryl group, a C6-C20 aryloxy group, a C2-C20 acyl group or a cyano group, and the C1-C20 alkyl group, the C1-C20 alkoxy group, the C6-C20 aryl group, the C6-C20 aryloxy group and the C2-C20 acyl group may be substituted with at least one substituent selected from the group consisting of a fluorine atom, a cyano group, a C1-C20 alkoxy group, a C6-C20 aryl group and a C6-C20 aryloxy group, and when multiple $R^1$s exist, $R^1$s may be the same groups or different groups, and the neighboring two $R^1$s may be bonded to form a ring,
$X^1$ represents a chlorine atom, a bromine atom or an iodine atom, and k represents an integer of 0 to 3,
a polyarylene comprising a repeating unit represented by the formula (2):

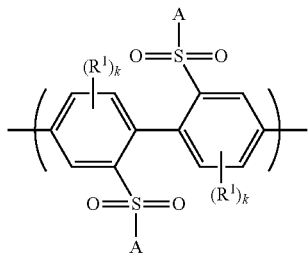

(2)

wherein A, $R^1$ and k represent the same meanings as defined above,
a process for producing the above-mentioned polyarylene, a process for producing a polyarylene comprising a repeating unit represented by the formula (7):

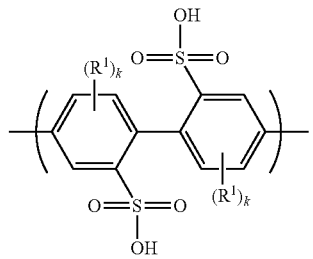

(7)

wherein $R^1$ and k represent the same meanings as defined above, from the above-mentioned polyarylene, and
a process for producing the above-mentioned dihalobiphenyl compound represented by the formula (1).

BEST MODE FOR CARRYING OUT THE PRESENT INVENTION

First, a dihalobiphenyl compound represented by the formula (1):

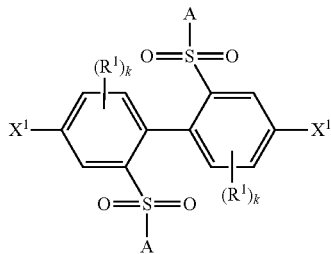

(1)

(hereinafter, simply referred to as the dihalobiphenyl compound (1)) will be illustrated.

A represents an amino group substituted with one or two C1-C20 hydrocarbon groups or a C1-C20 alkoxy group.

Examples of the hydrocarbon group include a C1-C20 hydrocarbon group such as a methyl group, an ethyl group, an n-propyl group, an isopropyl group, an n-butyl group, an isobutyl group, a sec-butyl group, a tert-butyl group, an n-pentyl group, a 2,2-methylpropyl group, an n-hexyl group, a cyclohexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosyl group, a phenyl group, a 1,3-butadiene-1,4-diyl group, a butane-1,4-diyl group, a pentane-1,5-diyl group, a biphenyl-2,2'-diyl group and an o-xylylene group.

Examples of the amino group substituted with one or two C1-C20 hydrocarbon groups include a methylamino group, a dimethylamino group, an ethylamino group, a diethylamino group, an n-propylamino group, a di-n-propylamino group, an isopropylamino group, a diisopropylamino group, an n-butylamino group, a di-n-butylamino group, a sec-butylamino group, a di-sec-butylamino group, a tert-butylamino group, a di-tert-butylamino group, an n-pentylamino group, a 2,2-dimethylpropylamino group, an n-hexylamino group, a cyclohexylamino group, an n-heptylamino group, an n-octylamino group, an n-nonylamino group, an n-decylamino group, an n-undecylamino group, an n-dodecylamino group, an n-tridecylamino group, an n-tetradecylamino group, an n-pentadecylamino group, an n-hexadecylamino group, an n-heptadecylamino group, an n-octadecylamino group, an n-nonadecylamino group, an n-icosylamino group, a pyrrolyl group, a pyrrolidinyl group, a piperidinyl group, a carbazolyl group, a dihydroindolyl group and a dihydroisoindolyl group, and the diethylamino group and the n-dodecylamino group are preferable.

Examples of the C1-C20 alkoxy group include a linear, branched chain or cyclic C3-C20 alkoxy group such as a methoxy group, an ethoxy group, a n-propoxy group, an isopropoxy group, an n-butoxy group, a sec-butoxy group, a tert-butoxy group, an n-pentyloxy group, a 2,2-dimethylpropoxy group, an n-hexyloxy group, a cyclohexyloxy group, an n-heptyloxy group, an n-octyloxy group, an n-nonyloxy group, an n-decyloxy group, an n-undecyloxy group, an n-dodecyloxy group, an n-tridecyloxy group, an n-tetradecyloxy group, an n-pentadecyloxy group, an n-hexadecyloxy group, an n-heptadecyloxy group, an n-octadecyloxy group, an n-nonadecyloxy group and an n-icosyloxy group, and the isopropoxy group, the 2,2-dimethypropoxy group and the cyclohexyloxy group are preferable.

The above-mentioned C1-C20 hydrocarbon group and the C1-C20 alkoxy group may be substituted with at least one group selected from the group consisting of a fluorine atom, a C1-C20 alkoxy group, a C6-C20 aryl group, a C6-C20 aryloxy group, a C2-C20 acyl group and a cyano group.

Examples of the C1-C20 alkoxy group include a linear, branched chain or cyclic C1-C20 alkoxy group such as a methoxy group, an ethoxy group, an n-propoxy group, an isopropoxy group, an n-butoxy group, an isobutoxy group, a sec-butoxy group, a tert-butoxy group, an n-pentyloxy group, a 2,2-methylpropoxy group, a cyclopentyloxy group, an n-hexyloxy group, a cyclohexyloxy group, an n-heptyloxy group, a 2-methylpentyloxy group, an n-octyloxy group, a 2-ethylhexyloxy group, an n-nonyloxy group, an n-decyloxy group, an n-undecyloxy group, an n-dodecyloxy group, an n-tridecyloxy group, an n-tetradecyloxy group, an n-pentadecyloxy group, an n-hexadecyloxy group, an n-heptadecyloxy group, an n-octadecyloxy group, an n-nonadecyloxy group and n-icosyloxy group.

Examples of the C6-C20 aryl group include a phenyl group, a 1-naphthyl group, a 2-naphthyl group, a 3-phenanthryl group and a 2-anthryl group. Examples of the C6-C20 aryloxy group include those composed of the above-mentioned C6-C20 aryl group and an oxygen atom such as a phenoxy group, a 1-naphthyloxy group, a 2-naphthyloxy group, a 3-phenanthryloxy group and a 2-anthryloxy group.

Examples of the C2-C20 acyl group include a C2-C20 aliphatic or aromatic acyl group such as an acetyl group, a propionyl group, a butyryl group, an isobutyryl group, a benzoyl group, a 1-naphthoyl group and a 2-naphthoyl group.

Among them, a C3-C20 unsubstituted alkoxy group is preferable as A, and the isopropyl group, the isobutoxy group, the 2,2-dimethylpropoxy group and the cyclohexyloxy group are more preferable.

$R^1$ represents a fluorine atom, a C1-C20 alkyl group, a C1-C20 alkoxy group, a C6-C20 aryl group, a C6-C20 aryloxy group, a C2-C20 acyl group or a cyano group.

Examples of the C1-C20 alkyl group include a linear, branched chain or cyclic C1-C20 alkyl group such as a methyl group, an ethyl group, an n-propyl group, an isopropyl group, an n-butyl group, an isobutyl group, a sec-butyl group, a tert-butyl group, an n-pentyl group, a 2,2-methylpropyl group, a cyclopentyl group, an n-hexyl group, a cyclohexyl group, an n-heptyl group, a 2-methylpentyl group, an n-octyl group, a 2-ethylhexyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group and an n-icosyl group.

Examples of the C1-C20 alkoxy group, the C6-C20 aryl group, the C6-C20 aryloxy group and the C2-C20 acyl group include those as same as described above.

The C1-C20 alkyl group, the C1-C20 alkoxy group, the C6-C20 aryl group, the C6-C20 aryloxy group and the C2-C20 acyl group may be substituted with at least one substituent selected from the group consisting of a fluorine atom, a cyano group, a C1-C20 alkoxy group, a C6-C20 aryl group and a C6-C20 aryloxy group, and examples of the C1-C20 alkoxy group, the C6-C20 aryl group and the C6-C20 aryloxy group include those as same as described above.

When multiple $R^1$s exist, $R^1$s may be the same groups or different groups. Alternatively, the neighboring two $R^1$s may be bonded to form a ring.

$X^1$ represents a chlorine atom, a bromine atom or an iodine atom, and the chlorine atom and the bromine atom are preferable, and k represents an integer of 0 to 3, and k preferably represents 0.

Examples of the dihalobiphenyl compound (1) include dimethyl 4,4'-dichlorobiphenyl-2,2'-disulfonate, diethyl 4,4'-dichlorobiphenyl-2,2'-disulfonate, di(n-propyl) 4,4'-dichlorobiphenyl-2,2'-disulfonate, diisopropyl 4,4'-dichlorobiphenyl-2,2'-disulfonate, di(n-butyl) 4,4'-dichlorobiphenyl-2,2'-disulfonate, diisobutyl 4,4'-dichlorobiphenyl-2,2'-disulfonate, di(2,2-dimethylpropyl) 4,4'-dichlorobiphenyl-2,2'-disulfonate, dicyclohexyl 4,4'-dichlorobiphenyl-2,2'-disulfonate, di(n-octyl) 4,4'-dichlorobiphenyl-2,2'-disulfonate, di(n-pentadecyl) 4,4'-dichlorobiphenyl-2,2'-disulfonate, di(n-icosyl) 4,4'-dichlorobiphenyl-2,2'-disulfonate, N,N-dimethyl-4,4'-dichlorobiphenyl-2,2'-disulfonamide, N,N-diethyl-4,4'-dichlorobiphenyl-2,2'-disulfonamide, N,N-di(n-propyl)-4,4'-dichlorobiphenyl-2,2'-disulfonamide, N,N-diisopropyl-4,4'-dichlorobiphenyl-2,2'-disulfonamide, N,N-di(n-butyl)-4,4'-dichlorobiphenyl-2,2'-disulfonamide, N,N-diisobutyl-4,4'-dichlorobiphenyl-2,2'-disulfonamide, N,N-di(2,2-dimethylpropyl)-4,4'-dichlorobiphenyl-2,2'-disulfonamide, N,N-di(n-octyl)-4,4'-dichlorobiphenyl-2,2'-disulfonamide, N,N-di(n-pentadecyl)-4,4'-dichlorobiphenyl-2,2'-disulfonamide, N,N-di(n-icosyl)-4,4'-dichlorobiphenyl-2,2'-disulfonamide, N,N-diphenyl-4,4'-dichlorobiphenyl-2,2'-disulfonamide, di(2,2-dimethylpropyl) 3,3'-dimethyl-4,4'-dichlorobiphenyl-2,2'-disulfonate, di(2,2-dimethylpropyl) 5,5'-dimethyl-4,4'-dichlorobiphenyl-2,2'-disulfonate, di(2,2-dimethylpropyl) 6,6'-dimethyl-4,4'-dichlorobiphenyl-2,2'-disulfonate, di(2,2-dimethylpropyl) 3,3'-dimethoxy-4,4'-dichlorobiphenyl-2,2'-disulfonate, di(2,2-dimethylpropyl) 5,5'-dimethoxy-4,4'-dichlorobiphenyl-2,2'-disulfonate, di(2,2-dimethylpropyl) 6,6'-dimethoxy-4,4'-dichlorobiphenyl-2,2'-disulfonate, di(2,2-dimethylpropyl) 3,3'-diphenyl-4,4'-dichlorobiphenyl-2,2'-disulfonate, di(2,2-dimethylpropyl) 3,3'-diacetyl-4,4'-dichlorobiphenyl-2,2'-disulfonate, di(2,2-dimethylpropyl) 5,5'-diacetyl-4,4'-dichlorobiphenyl-2,2'-disulfonate, dimethyl 4,4'-dibromobiphenyl-2,2'-disulfonate, diethyl 4,4'-dibromobiphenyl-2,2'-disulfonate, di(n-propyl) 4,4'-dibromobiphenyl-2,2'-disulfonate, diisopropyl 4,4'-dibromobiphenyl-2,2'-disulfonate, di(n-butyl) 4,4'-dibromobiphenyl-2,2'-disulfonate, diisobutyl 4,4'-dibromobiphenyl-2,2'-disulfonate, di(2,2-dimethylpropyl) 4,4'-dibromobiphenyl-2,2'-disulfonate, dicyclohexyl 4,4'-dibromobiphenyl-2,2'-disulfonate, di(n-octyl) 4,4'-dibromobiphenyl-2,2'-disulfonate, di(n-pentadecyl) 4,4'-dibromobiphenyl-2,2'-disulfonate, di(n-icosyl) 4,4'-dibromobiphenyl-2,2'-disulfonate, N,N-dimethyl-4,4'-dibromobiphenyl-2,2'-disulfonamide, N,N-diethyl-4,4'-dibromobiphenyl-2,2'-disulfonamide, N,N-di(n-propyl)-4,4'-dibromobiphenyl-2,2'-disulfonamide, N,N-diisopropyl-4,4'-dibromobiphenyl-2,2'-disulfonamide, N,N-di(n-butyl)-4,4'-dibromobiphenyl-2,2'-disulfonamide, N,N-diisobutyl-4,4'-dibromobiphenyl-2,2'-disulfonamide, N,N-di(2,2-dimethylpropyl)-4,4'-dibromobiphenyl-2,2'-disulfonamide, N,N-di(n-octyl)-4,4'-dibromobiphenyl-2,2'-disulfonamide, N,N-di(n-pentadecyl)-4,4'-dibromobiphenyl-2,2'-disulfonamide, N,N-di(n-icosyl)-4,4'-dibromobiphenyl-2,2'-disulfonamide, and N,N-diphenyl-4,4'-dibromobiphenyl-2,2'-disulfonamide.

Among them, diisopropyl 4,4'-dichlorobiphenyl-2,2'-disulfonate, di(2,2-dimethylpropyl) 4,4'-dichlorobiphenyl-2,2'-disulfonate, diisopropyl 4,4'-dibromobiphenyl-2,2'-disulfonate and di(2,2-dimethylpropyl) 4,4'-dibromobiphenyl-2,2'-disulfonate are preferable.

A polyarylene can be produced by polymerizing a monomer composition comprising the dihalobiphenyl compound (1). Alternatively, a polyarylene can also be produced by polymerizing the dihalobiphenyl compound (1) only. The polyarylene and the process for producing the same will be illustrated below.

Specific examples of the polyarylene include a polyarylene comprising a repeating unit represented by the formula (2):

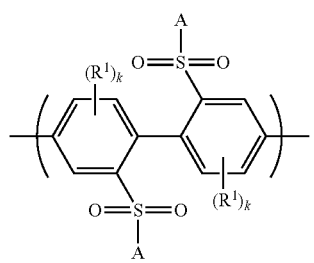

(2)

wherein A, $R^1$ and k represent the same meanings as defined above (hereinafter, simply referred to as the repeating unit (2)), a polyarylene consisting of the above-mentioned repeating unit (2),
a polyarylene comprising the above-mentioned repeating unit (2) and a segment represented by the formula (3):

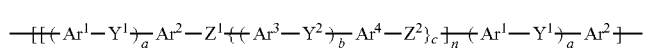

(3)

wherein a, b and c are the same or different, and each represents 0 or 1, and n represents an integer of 5 or more, $Ar^1$, $Ar^2$, $Ar^3$ and $Ar^4$ are the same or different, and each represents a divalent aromatic group, and the divalent aromatic group may be substituted with at least one substituent selected from the group consisting of a C1-C20 alkyl group which may be substituted with at least one substituent selected from the group consisting of a fluorine atom, a cyano group, a C1-C20 alkoxy group, a C6-C20 aryl group and a C6-C20 aryloxy group;

a C1-C20 alkoxy group which may be substituted with at least one substituent selected from the group consisting of a fluorine atom, a cyano group, a C1-C20 alkoxy group, a C6-C20 aryl group and a C6-C20 aryloxy group;

a C6-C20 aryl group which may be substituted with at least one substituent selected from the group consisting of a fluorine atom, a cyano group, a C1-C20 alkoxy group and a C6-C20 aryloxy group;

a C6-C20 aryloxy group which may be substituted with at least one substituent selected from the group consisting of a fluorine atom, a cyano group, a C1-C20 alkoxy group and a C6-C20 aryloxy group; and a C2-C20 acyl group which may be substituted with at least one substituent selected from the group consisting of a fluorine atom, a cyano group, a C1-C20 alkoxy group, a C6-C20 aryl group and a C6-C20 aryloxy group,
$Y^1$ and $Y^2$ are the same or different, and each represents a single bond, a carbonyl group, a sulfonyl group, a 2,2-isopropylidene group, a 2,2-hexafluoroisopropylidene group or a fluorene-9,9-diyl group, and
$Z^1$ and $Z^2$ are the same or different, and each represents an oxygen atom or a sulfur atom (hereinafter, simply referred to as the segment (3)), and
a polyarylene comprising the above-mentioned repeating unit (2) and a repeating unit represented by the formula (4):

—$Ar^5$—       (4)

wherein $Ar^5$ represents a divalent aromatic group, and the divalent aromatic group may be substituted with at least one substituent selected from the group consisting of a C1-C20 alkyl group which may be substituted with at least one substituent selected from the group consisting of a fluorine atom, a cyano group, a C1-C20 alkoxy group, a C6-C20 aryl group and a C6-C20 aryloxy group;

a C1-C20 alkoxy group which may be substituted with at least one substituent selected from the group consisting of a fluorine atom, a cyano group, a C1-C20 alkoxy group, a C6-C20 aryl group and a C6-C20 aryloxy group;

a C6-C20 aryl group which may be substituted with at least one substituent selected from the group consisting of a fluorine atom, a cyano group, a C1-C20 alkoxy group and a C6-C20 aryloxy group;

a C6-C20 aryloxy group which may be substituted with at least one substituent selected from the group consisting of a fluorine atom, a cyano group, a C1-C20 alkoxy group and a C6-C20 aryloxy group; and a C2-C20 acyl group which may be substituted with at least one substituent selected from the group consisting of a fluorine atom, a cyano group, a C1-C20 alkoxy group, a C6-C20 aryl group and a C6-C20 aryloxy group (hereinafter, simply referred to as the repeating unit (4)).

In the polyarylene comprising the repeating unit (2), at least two repeating units (2) are usually continued.

The polyarylene comprising the repeating unit (2) may have a repeating unit(s) or a segment(s) other than the repeating unit (2). The polyarylene comprising the repeating unit (2) and the segment (3) may be a polyarylene consisting of the repeating unit (2) and the segment (3), and may have a repeating unit(s) or a segment(s) other than the repeating unit (2) and the segment (3) in addition to the repeating unit (2) and the segment (3). The polyarylene comprising the repeating units (2) and (4) may be a polyarylene consisting of the repeating units (2) and (4), and may have a repeating unit(s) and a segment(s) other than the repeating units (2) and (4) in addition to the repeating units (2) and (4).

The weight average molecular weight of these polyarylenes in terms of polystyrene is usually 1,000 to 2,000,000. When these polyarylenes are used as a polyelectrolyte for proton-exchange membrane fuel cell, preferable weight average molecular weight thereof is 2,000 to 1,000,000 and more preferable one is 3,000 to 800,000.

Specific examples of the repeating unit (2) include repeating units represented by the following formulae (2a) to (2d):

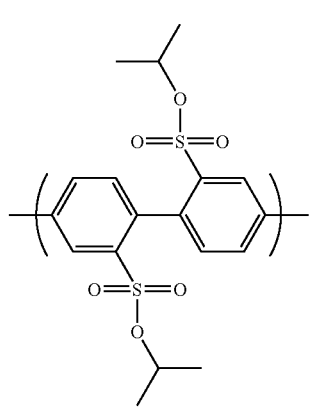

(2a)

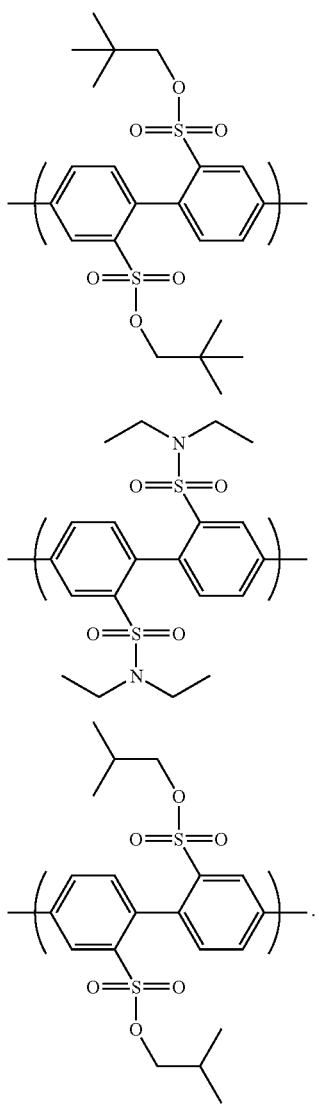

Examples of the divalent aromatic group in the segment (3) include a divalent monocyclic aromatic group such as a 1,3-phenylene group and a 1,4-phenylene group; a divalent condensed ring type aromatic group such as a naphthalene-1,3-diyl group, a naphthalene-1,4-diyl group, a naphthalene-1,5-diyl group, a naphthalene-1,6-diyl group, a naphthalene-1,7-diyl group, a naphthalene-2,6-diyl group and a naphthalene-2,7-diyl group; and a divalent heteroaromatic group such as a pyridine-2,5-diyl group, a pyridine-2,6-diyl group, a quinoxaline-2,6-diyl group and a thiophene-2,5-diyl group. Among them, the divalent monocyclic aromatic group and the divalent condensed ring type aromatic group are preferable, and the 1,4-phenylene group, the naphthalene-1,4-diyl group, the naphthalene-1,5-diyl group, the naphthalene-2,6-diyl group and the naphthalene-2,7-diyl group are more preferable.

The above-mentioned divalent aromatic group may be substituted with at least one substituent selected from the group consisting of a C1-C20 alkyl group which may be substituted with at least one substituent selected from the group consisting of a fluorine atom, a cyano group, a C1-C20 alkoxy group, a C6-C20 aryl group and a C6-C20 aryloxy group; a C1-C20 alkoxy group which may be substituted with at least one substituent selected from the group consisting of a fluorine atom, a cyano group, a C1-C20 alkoxy group, a C6-C20 aryl group and a C6-C20 aryloxy group; a C6-C20 aryl group which may be substituted with at least one substituent selected from the group consisting of a fluorine atom, a cyano group, a C1-C20 alkoxy group and a C6-C20 aryloxy group; a C6-C20 aryloxy group which may be substituted with at least one substituent selected from the group consisting of a fluorine atom, a cyano group, a C1-C20 alkoxy group and a C6-C20 aryloxy group; and a C2-C20 acyl group which may be substituted with at least one substituent selected from the group consisting of a fluorine atom, a cyano group, a C1-C20 alkoxy group, a C6-C20 aryl group and a C6-C20 aryloxy group.

Examples of the C1-C20 alkyl group, the C1-C20 alkoxy group, the C6-C20 aryl group, the C6-C20 aryloxy group and the C2-C20 acyl group include the same as described above.

Specific examples of the segment (3) include segments represented by the following formulae (3a) to (3y), and in the following formulae, n represents the same meaning as defined above, and n is preferably 5 or more, and more preferably 10 or more. The weight average molecular weight of the segment (3) in terms of polystyrene is usually 2,000 or more, and preferably 3,000 or more.

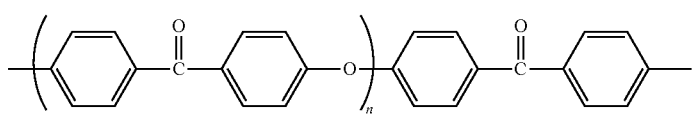

(3a)

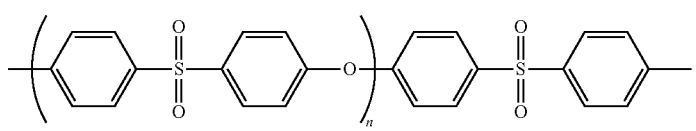

(3b)

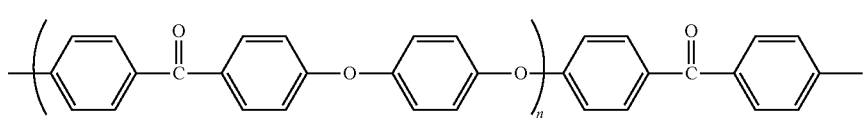

(3c)

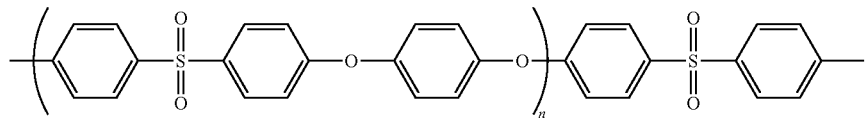
(3d)
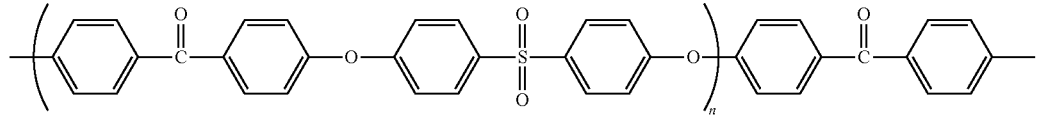
(3e)
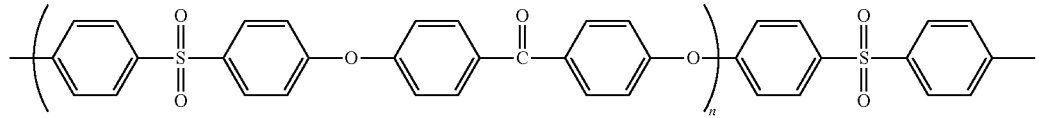
(3f)
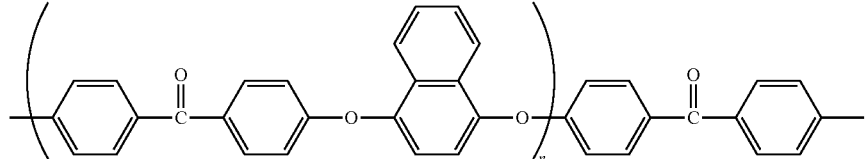
(3g)
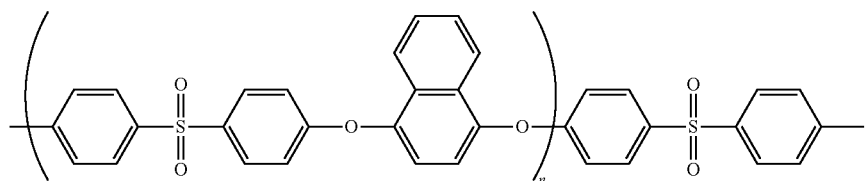
(3h)
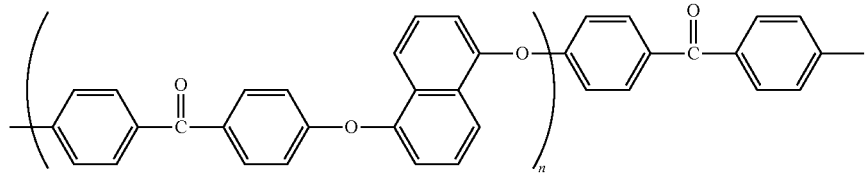
(3i)
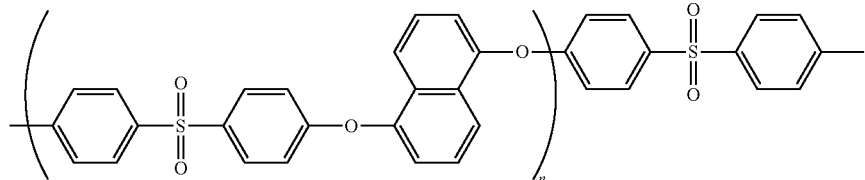
(3j)
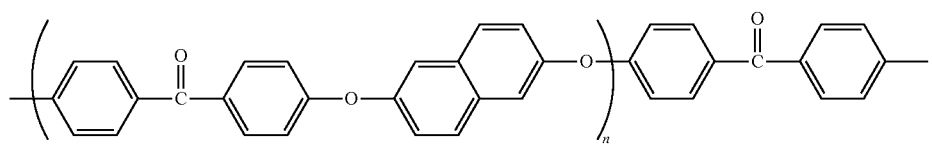
(3k)
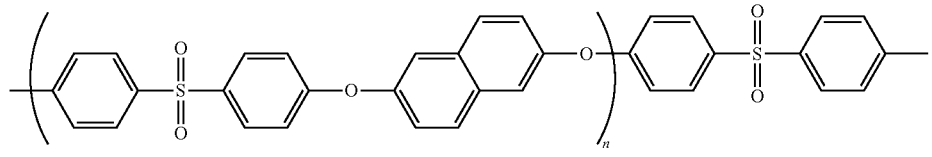
(3l)
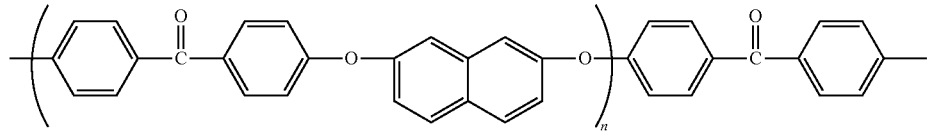
(3m)

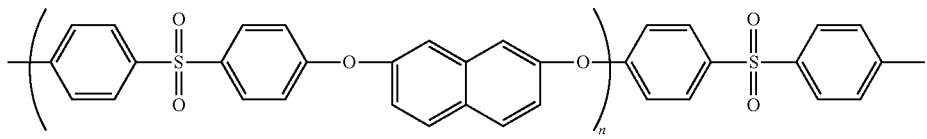
(3n)
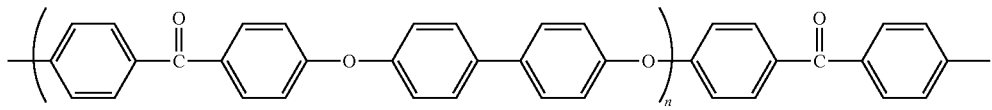
(3o)
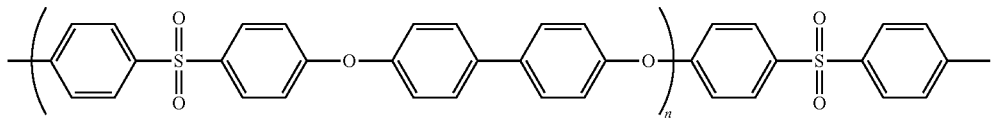
(3p)
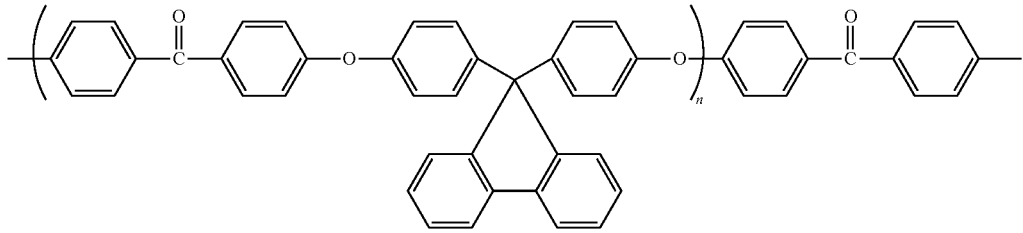
(3q)
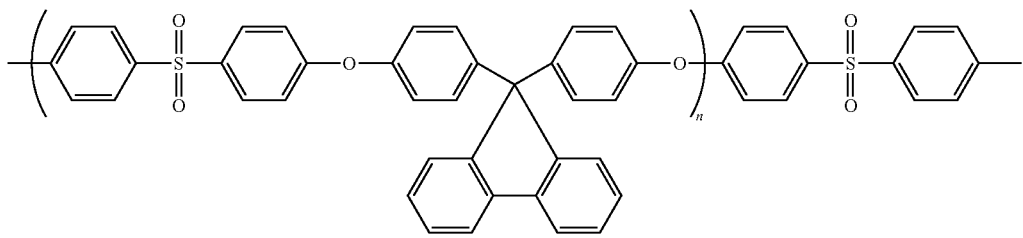
(3r)
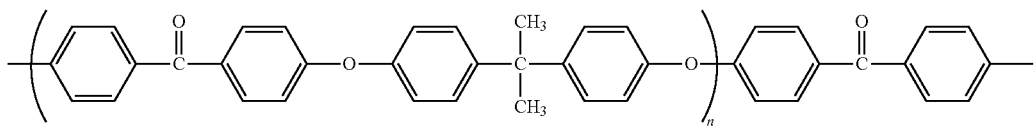
(3s)
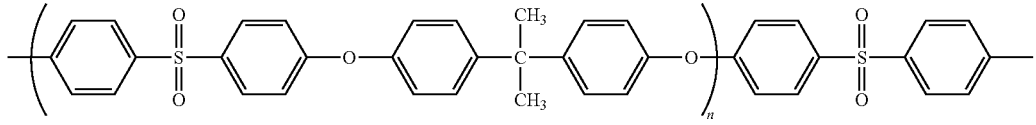
(3t)
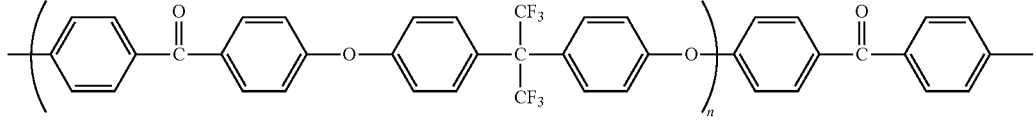
(3u)
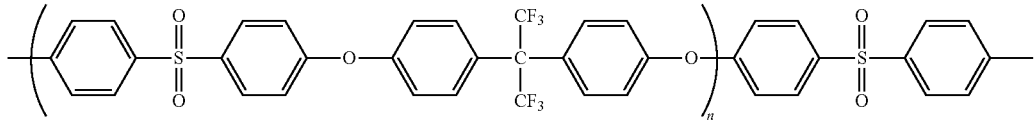
(3v)

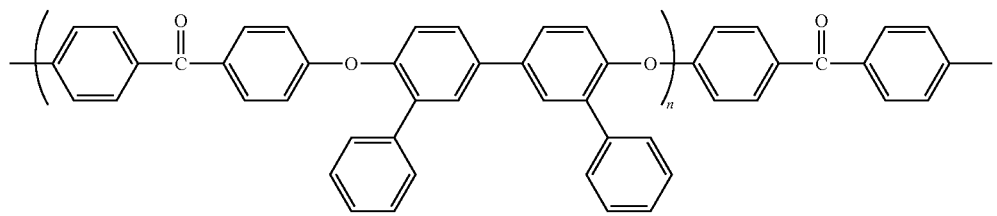

(3x)

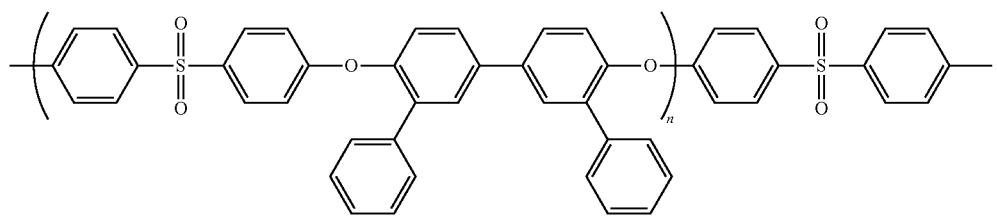

(3y)

Examples of the polyarylene comprising the repeating unit (2) and the segment (3) include a polyarylene comprising any one of the above-mentioned repeating units represented by the formulae (2a) to (2d) and any one of the above-mentioned segments represented by the formulae (3a) to (3y). Specifically, polyarylenes represented by the following formulae (1) to (III) are exemplified. In the following formulae, n represents the same meaning as defined above and p represents an integer of 2 or more.

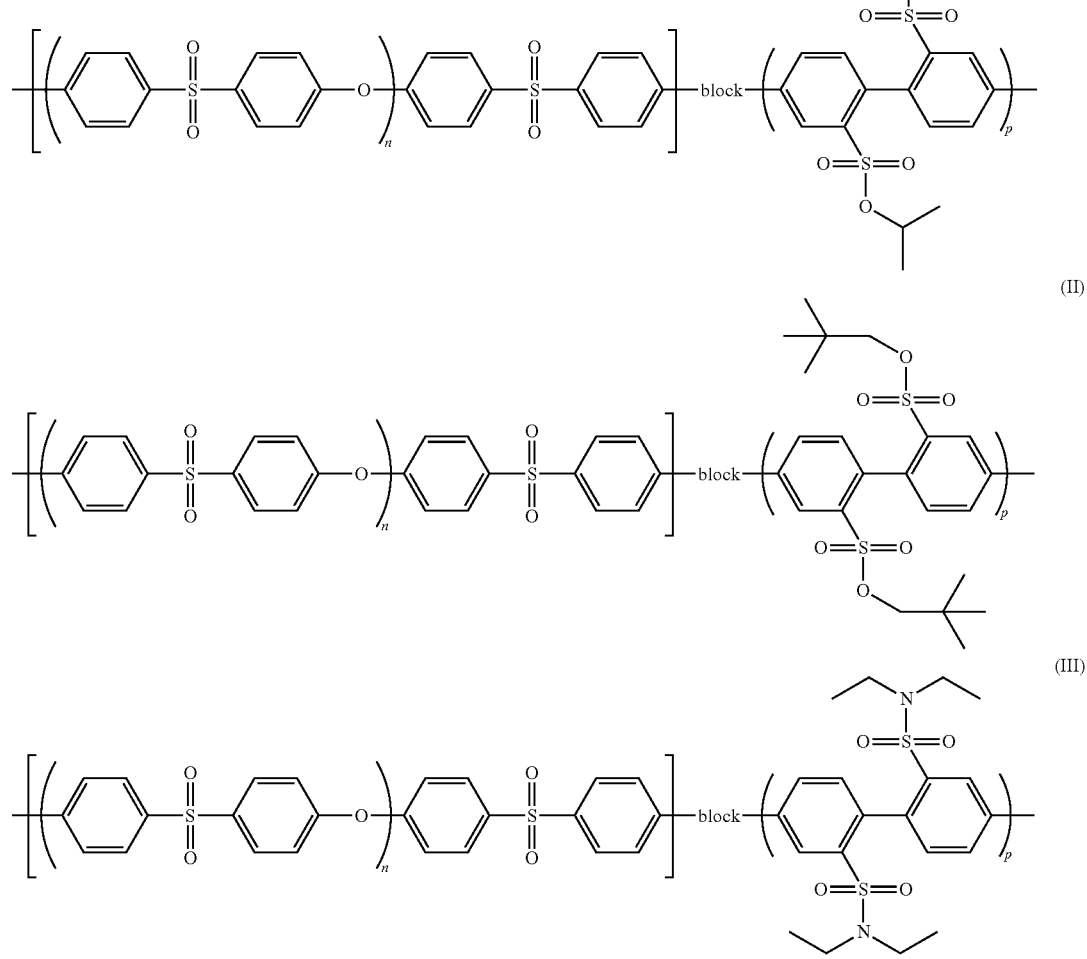

The amount of the repeating unit (2) in the polyarylene comprising the repeating unit (2) and the segment (3) is preferably 5% by weight or more and 95% by weight or less, and more preferably 30% by weight or more and 90% by weight or less. The amount of the segment (3) in the polyarylene comprising the repeating unit (2) and the segment (3) is preferably 5% by weight or more and 95% by weight or less, and more preferably 10% by weight or more and 70% by weight or less.

Examples of the divalent aromatic group in the repeating unit (4) include the same as the divalent aromatic group in the segment (3) described above. The divalent aromatic group may be substituted with at least one substituent selected from the group consisting of a C1-C20 alkyl group which may be substituted with at least one substituent selected from the group consisting of a fluorine atom, a cyano group, a C1-C20 alkoxy group, a C6-C20 aryl group and a C6-C20 aryloxy group; a C1-C20 alkoxy group which may be substituted with at least one substituent selected from the group consisting of a fluorine atom, a cyano group, a C1-C20 alkoxy group, a C6-C20 aryl group and a C6-C20 aryloxy group; a C6-C20 aryl group which may be substituted with at least one substituent selected from the group consisting of a fluorine atom, a cyano group, a C1-C20 alkoxy group and a C6-C20 aryloxy group; a C6-C20 aryloxy group which may be substituted with at least one substituent selected from the group consisting of a fluorine atom, a cyano group, a C1-C20 alkoxy group and a C6-C20 aryloxy group; and a C2-C20 acyl group which may be substituted with at least one substituent selected from the group consisting of a fluorine atom, a cyano group, a C1-C20 alkoxy group, a C6-C20 aryl group and a C6-C20 aryloxy group. Examples of the C1-C20 alkyl group, the C1-C20 alkoxy group, the C6-C20 aryl group, the C6-C20 aryloxy group and the C2-C20 acyl group include the same as described above.

Specific examples of the repeating unit (4) include repeating units represented by the following formulae (4a) and (4b).

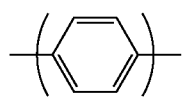

(4a)

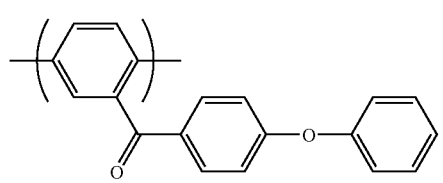

(4b)

Examples of the polyarylene comprising the repeating units (2) and (4) include polyarylenes comprising any one of the above-mentioned repeating units represented by the formulae (2a) to (2c) and any one of the above-mentioned repeating units represented by the formulae (4a) to (4b). Specifically, polyarylenes represented by the following formulae (IV) to (VII) are exemplified.

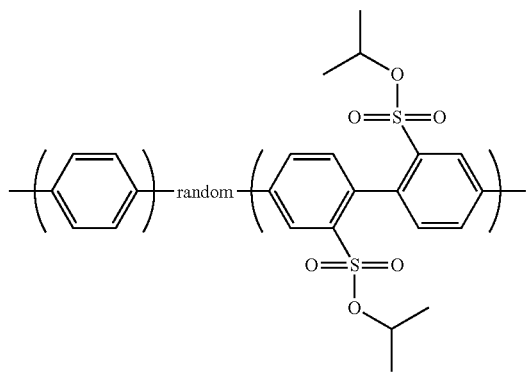

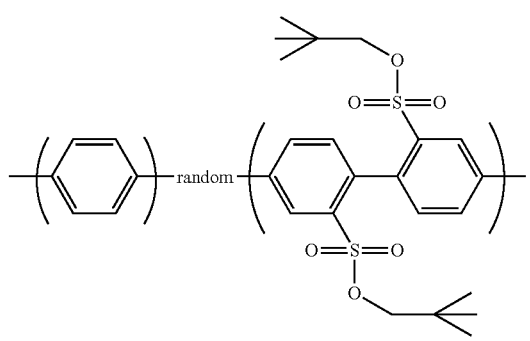

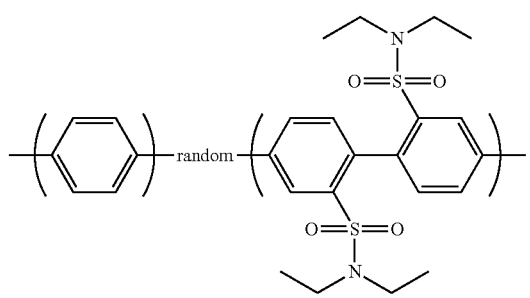

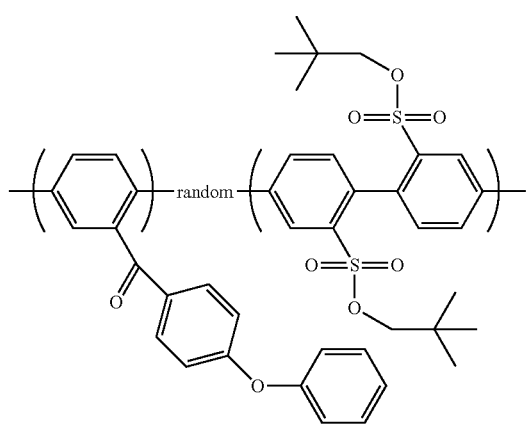

The amount of the repeating unit (2) in the polyarylene comprising the repeating units (2) and (4) is preferably 5% by weight or more and 95% by weight or less, and more preferably 30% by weight or more and 90% by weight or less. The amount of the repeating unit (4) in the polyarylene comprising the repeating units (2) and (4) is preferably 5% by weight or more and 95% by weight or less, and more preferably 10% by weight or more and 70% by weight or less.

The polyarylene comprising the repeating unit (2) can be produced by polymerizing a monomer composition comprising the dihalobiphenyl compound (1) in the presence of a nickel compound. The polyarylene consisting of the repeating unit (2) can be produced by polymerizing the dihalobiphenyl compound (1) only in the presence of a nickel compound. The polyarylene comprising the repeating unit (2) and the segment (3) can be produced by polymerizing a monomer composition comprising the dihalobiphenyl compound (1) and a compound represented by the formula (5):

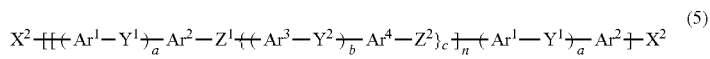
(5)

wherein a, b, c, n, $Ar^1$, $Ar^2$, $Ar^3$, $Ar^4$, $Y^1$, $Y^2$, $Z^1$ and $Z^2$ are the same meanings as defined above and $X^2$ represents a chlorine atom, a bromine atom or an iodine atom (hereinafter, simply referred to as the compound (5)), in the presence of a nickel compound. Alternatively, the polyarylene comprising the repeating unit (2) and the segment (3) can also be produced by polymerizing the dihalobiphenyl compound (1) only in the presence of a nickel compound and then further conducting a polymerization reaction by adding the compound (5).

The polyarylene comprising the repeating units (2) and (4) can be produced by polymerizing a monomer composition comprising the dihalobiphenyl compound (1) and a compound represented by the formula (6):

$$X^3—Ar^5—X^3 \qquad (6)$$

wherein $Ar^5$ is the same meaning as defined above and $X^3$ represents a chlorine atom, a bromine atom or an iodine atom (hereinafter, simply referred to as the compound (6)), in the presence of a nickel compound.

Examples of the compound (5) include the following compounds and the following compounds wherein the terminal chlorine atoms are substituted with bromine atoms.

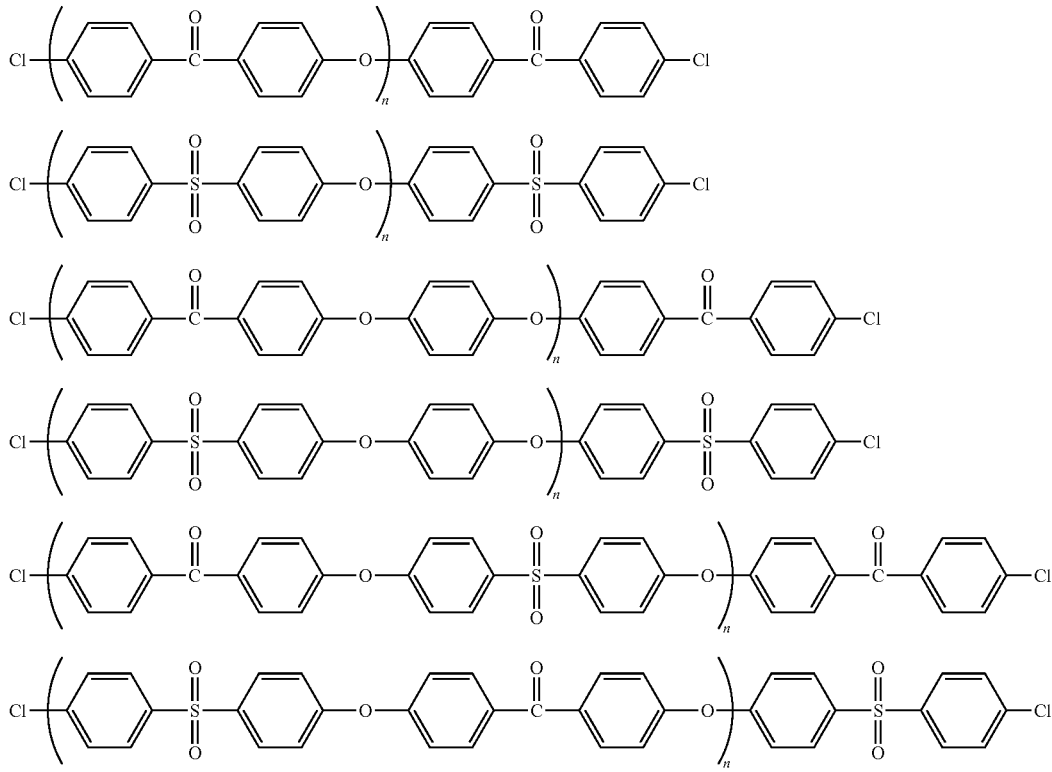

-continued
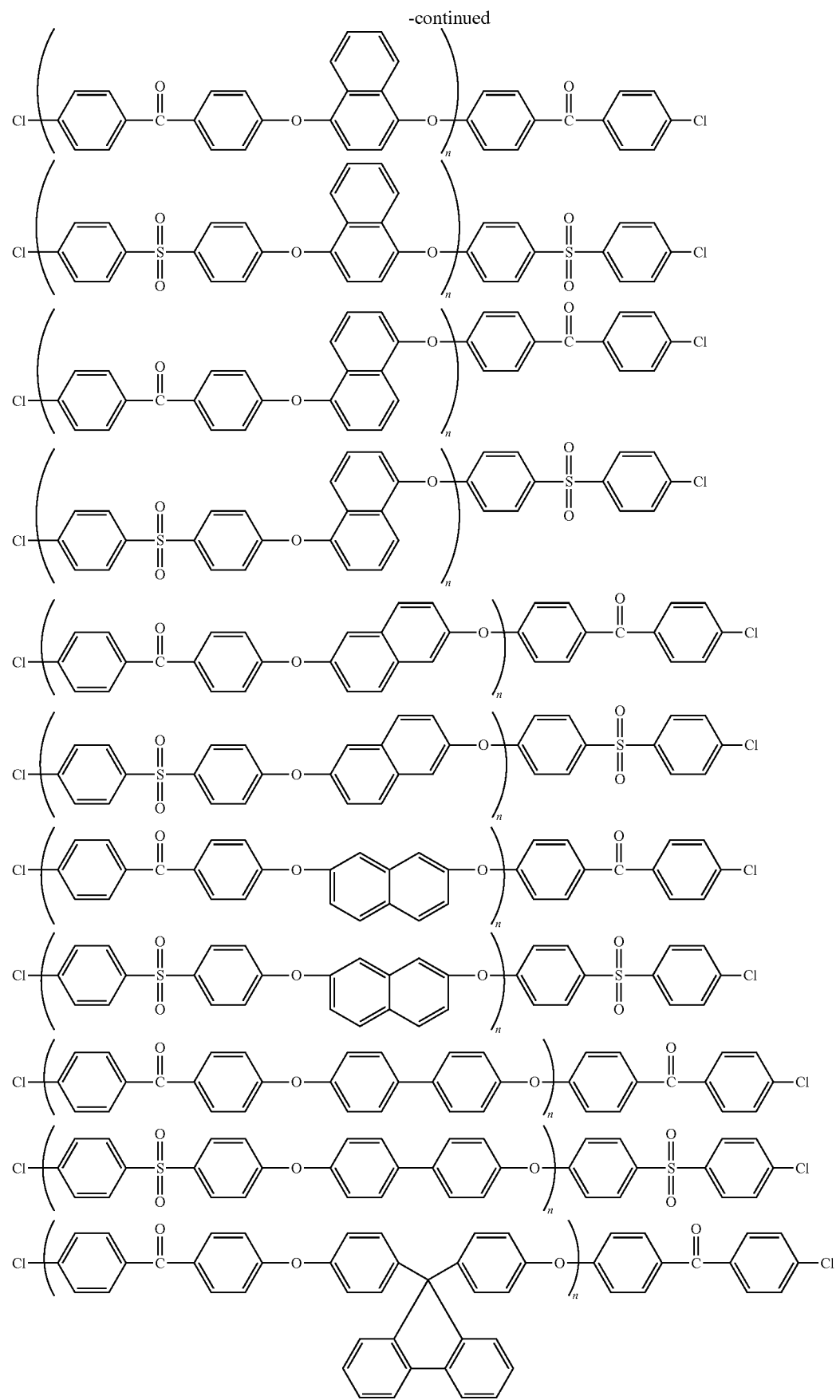

-continued

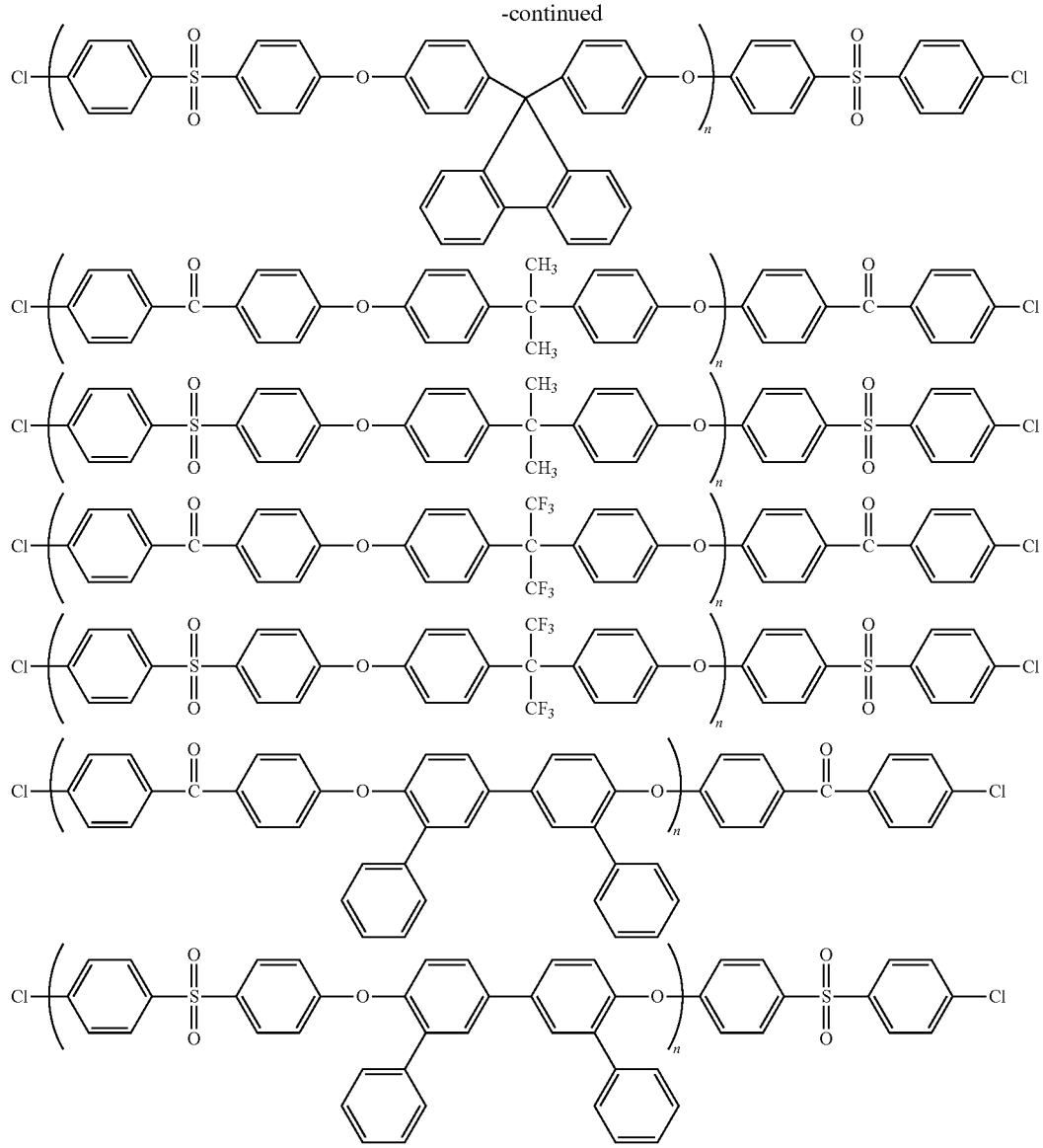

As the compound (5), for example, one produced according to known methods such as JP Patent No. 2745727 may be used or a commercially available one may be used. Examples of the commercially available one include SUMIKA EXCEL PES manufactured by Sumitomo Chemical Company, Limited.

As the compound (5), one having 2,000 or more of weight average molecular weight in terms of polystyrene is preferably used, and one having 3,000 or more of weight average molecular weight in terms of polystyrene is more preferably used.

Examples of the compound (6) include 1,3-dichlorobenzene, 1,4-dichlorobenzene, 1,3-dibromobenzene, 1,4-dibromobenzene, 1,3-diiodobenzene, 1,4-diiodobenzene, 2,4-dichlorotoluene, 2,5-dichlorotoluene, 3,5-dichlorotoluene, 2,4-dibromotoluene, 2,5-dibromotoluene, 3,5-dibromotoluene, 2,4-diiodotoluene, 2,5-diiodotoluene, 3,5-diiodotoluene, 1,3-dichloro-4-methoxybenzene, 1,4-dichloro-3-methoxybenzene, 1,3-dibromo-4-methoxybenzene, 1,4-dibromo-3-methoxybenzene, 1,3-diiodo-4-methoxybenzene, 1,4-diiodo-3-methoxybenzene, 1,3-dichloro-4-acetoxybenzene, 1,4-dichloro-3-acetoxybenzene, 1,3-dibromo-4-acetoxybenzene, 1,4-dibromo-3-acetoxybenzene, 1,3-diiodo-4-acetoxybenzene, 1,4-diiodo-3-acetoxybenzene and 2,5-dichloro-4'-phenoxybenzophenone.

The content of the repeating unit (2) in the polyarylene obtained can be adjusted by adjusting arbitrarily the content of the dihalobiphenyl compound (1) in the monomer composition.

Examples of the nickel compound include a zerovalent nickel compound such as bis(cyclooctadiene)nickel (0), (ethylene)bis(triphenylphosphine)nickel (0) and tetrakis(triphenylphosphine)nickel (0), and a divalent nickel compound such as a nickel halide (e.g. nickel fluoride, nickel chloride, nickel bromide, nickel iodide etc.), a nickel carboxylate (e.g. nickel formate, nickel acetate etc.), nickel sulfate, nickel carbonate, nickel nitrate, nickel acetylacetonate and (dimethoxyethane)nickel chloride, and bis(cyclooctadiene) nickel (0) and the nickel halide are preferable.

When the amount of the nickel compound to be used is small, a polyarylene having a small molecular weight tends to be obtained, and when the amount thereof is high, a polyarylene having a large molecular weight tends to be obtained. Therefore, the amount of the nickel compound to be used may be decided depending on the desirable molecular weight of the polyarylene. The amount of the nickel compound to be used is usually 0.01 to 5 moles per 1 mole of the monomer in the monomer composition. Herein, the monomer in the monomer composition means a monomer(s) which is involved in the polymerization reaction and which is contained in the monomer composition such as the dihalobiphenyl compound, the compound (5), the compound (6) and the like.

The polymerization reaction is preferably conducted in the presence of the nickel compound and a nitrogen-containing bidentate ligand. Examples of the nitrogen-containing bidentate ligand include 2,2'-bipyridine, 1,10-phenanthroline, methylenebisoxazoline and N,N'-tetramethylethylenediamine, and 2,2'-bipyridine is preferable. When the nitrogen-containing bidentate ligand is used, the amount thereof is usually 0.2 to 2 moles, and preferably 1 to 1.5 moles per 1 mole of the nickel compound.

When the divalent nickel compound is used as the nickel compound, zinc is usually used together. As zinc, powdery one is usually used. When zinc is used, the amount thereof is usually 1 mole or more per 1 mole of the monomer in the monomer composition. While the upper limit is not particularly limited, when it is too much, it may be trouble in the aftertreatment after the polymerization reaction and it may also result in economical disadvantage, and therefore, it is practically 10 moles or less, and preferably 5 moles or less.

Alternatively, when the zerovalent nickel compound is used as the nickel compound and the amount of the zerovalent nickel compound is less than 1 mole per 1 mole of the monomer in the monomer composition, the polymerization reaction is conducted in the co-presence of zinc. The powdery zinc is usually used. When zinc is used, the amount thereof is usually 1 mole or more per 1 mole of the monomer in the monomer composition. While the upper limit is not particularly limited, when it is too much, it may be trouble in the aftertreatment after the polymerization reaction and it may also result in economical disadvantage, and therefore, it is practically 10 moles or less, and preferably 5 moles or less.

The polymerization reaction is usually carried out in the presence of a solvent. The solvent may be one in which the monomer composition and the polyarylene produced can be dissolved. Specific examples of the solvent include an aromatic hydrocarbon solvent such as toluene and xylene; an ether solvent such as tetrahydrofuran and 1,4-dioxane; an aprotic polar solvent such as dimethylsulfoxide, N-methylpyrrolidone, N,N-dimethylformamide, N,N-dimethylacetamide and hexamethylphosphoric triamide; and a halogenated hydrocarbon solvent such as dichloromethane and dichloroethane. These solvents may be used alone, and two or more thereof may be mixed each other to be used. Among them, the ether solvent and the aprotic polar solvent are preferable and tetrahydrofuran, dimethylsulfoxide, N-methyl-2-pyrrolidone and N,N-dimethylacetamide are more preferable. When the amount of the solvent is too large, a polyarylene having small molecular weight tends to be obtained, and when the amount thereof is too small, the property of the reaction mixture tends to be bad, and therefore, the amount thereof is usually 1 to 200 parts by weight and preferably 5 to 100 parts by weight per 1 parts by weight of the monomer in the monomer composition.

The polymerization reaction is usually conducted in an atmosphere of an inert gas such as nitrogen gas.

The polymerization temperature is usually 0 to 250° C., and preferably 30 to 100° C. The polymerization time is usually 0.5 to 48 hours.

After the completion of polymerization reaction, a polyarylene can be isolated by mixing a solvent in which the polyarylene produced is poorly soluble with the reaction mixture to precipitate the polyarylene and separating the polyarylene precipitated from the reaction mixture by filtration. A solvent in which the polyarylene produced is insoluble or poorly soluble may be mixed with the reaction mixture, and then an aqueous acid solution such as hydrochloric acid may be added thereto followed by separating the polyarylene precipitated by filtration. The molecular weight and the structure of the polyarylene obtained can be analyzed by a conventional means such as gel permeation chromatography and NMR. Examples of the solvent in which the polyarylene produced is insoluble or poorly soluble include water, methanol, ethanol and acetonitrile, and water and methanol are preferable.

Next, a process for converting the polyarylene comprising the repeating unit (2) to a polyarylene comprising a repeating unit represented by the formula (7):

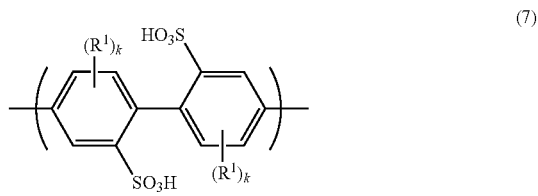

(7)

wherein $R^1$, m and k represent the same meanings as above (hereinafter, simply referred to as the repeating unit (7)), will be illustrated.

Examples of the process for converting the polyarylene comprising the repeating unit (2) to the polyarylene comprising the repeating unit (7) include a process comprising hydrolyzing the polyarylene comprising the repeating unit (2) in the presence of an acid or an alkali, and a process comprising reacting the polyarylene comprising the repeating unit (2) with an alkali metal halide or a quaternary ammonium halide followed by conducting an acid treatment.

The polyarylene consisting of the repeating unit (2) can be converted to the polyarylene consisting of the repeating unit (7) by thus process, and the polyarylene comprising the repeating unit (2) and the segment (3) can be converted to a polyarylene comprising the repeating unit (7) and the segment (3) by thus process. Alternatively, the polyarylene comprising the repeating units (2) and (4) can be converted to a polyarylene comprising the repeating units (7) and (4).

The process comprising hydrolyzing the polyarylene comprising the repeating unit (2) in the presence of an acid or an alkali will be illustrated below.

The hydrolysis reaction of the polyarylene comprising the repeating unit (2) is usually conducted by mixing the polyarylene comprising the repeating unit (2) with an aqueous acid or alkali solution. Examples of the aqueous acid solution include an aqueous solution of an inorganic acid such as hydrochloric acid, sulfuric acid and nitric acid, and examples of the aqueous alkali solution include an aqueous solution of an alkali metal hydroxide such as sodium hydroxide and potassium hydroxide. The aqueous acid solution is preferably used and hydrochloric acid is more preferably used. The amount of the acid or alkali to be used may be usually 1 mole or more per 1 mole of the group represented by —$SO_2A$ in the polyarylene comprising the repeating unit (2), and the upper limit thereof is not particularly limited.

The hydrolysis reaction may be conducted in the presence of a solvent, and examples of the solvent include a hydrophilic alcohol solvent such as methanol and ethanol. The amount of the solvent to be used is not particularly limited.

The hydrolysis temperature is usually 0 to 250° C. and preferably 40 to 120° C. The hydrolysis time is usually 1 to 150 hours.

The progress of the reaction can be checked by, for example, NMR, IR or the like.

When the polyarylene comprising the repeating unit (2) is hydrolyzed in the presence of the acid, the polyarylene comprising the repeating unit (7) is usually precipitated in the reaction mixture after completion of the hydrolysis reaction, and the polyarylene comprising the repeating unit (7) can be isolated by filtrating the reaction mixture. When the polyarylene comprising the repeating unit (2) is hydrolyzed in the presence of the alkali, the polyarylene comprising the repeating unit (7) can be isolated by mixing the reaction mixture with an acid to acidify the reaction mixture and to precipitate the polyarylene comprising the repeating unit (7) in the reaction mixture followed by filtrating the reaction mixture.

The polyarylene consisting of the repeating unit (7) is obtained by conducting the similar method to the above against the polyarylene consisting of the repeating unit (2). The polyarylene comprising the repeating unit (7) and the segment (3) is obtained by conducting the similar method to the above against the polyarylene comprising the repeating unit (2) and the segment (3). The polyarylene comprising the repeating unit (7) and the repeating unit (4) can be obtained by conducting the similar method to the above against the polyarylene comprising the repeating unit (2) and the segment (4).

Next, the process comprising reacting the polyarylene comprising the repeating unit (2) with the alkali metal halide or the quaternary ammonium halide followed by conducting an acid treatment will be illustrated.

Examples of the alkali metal halide include lithium bromide and sodium iodide, and examples of the quaternary ammonium halide include tetramethylammonium chloride and tetrabutylammonium bromide, and lithium bromide and tetrabutylammonium bromide are preferable.

The amount of the alkali metal halide or the quaternary ammonium halide to be used is usually 1 mole or more per 1 mole of the group represented by —SO$_2$A in the polyarylene comprising the repeating unit (2), and the upper limit thereof is not particularly limited.

The reaction of the polyarylene comprising the repeating unit (2) and the alkali metal halide or the quaternary ammonium halide is usually conducted by mixing the polyarylene comprising the repeating unit (2) with the alkali metal halide or the quaternary ammonium halide in the presence of a solvent. The solvent may be one that can be dissolve the polyarylene comprising the repeating unit (2) and examples of the solvent include the same as those used in the above-mentioned polymerization reaction. When the amount of the solvent to be used is small, the properties of the reaction mixture may tend to be bad, and when it is too much, the filterability of the polyarylene comprising the repeating unit (7) obtained may tend to be bad, and therefore, it is usually 1 to 200 parts by weight per 1 part of the polyarylene comprising the repeating unit (2), and preferably 5 to 50 parts by weight.

The reaction temperature is usually 0 to 250° C., and preferably 100 to 160° C. The reaction time is usually 1 to 150 hours.

The progress of the reaction can be checked by NMR, IR or the like.

After completion of the reaction, the polyarylene comprising the repeating unit (7) can be isolated by conducting the acid treatment of the reaction mixture followed by filtration.

The acid treatment is usually carried out by mixing the reaction mixture with an acid. Examples of the acid include hydrochloric acid and sulfuric acid. The amount of the acid to be used may be enough amounts to acidify the reaction mixture.

The polyarylene comprising the repeating unit (7) and the segment (3) is obtained by conducting the similar method to the above against the polyarylene comprising the repeating unit (2) and the segment (3). The polyarylene comprising the repeating units (7) and (4) can be obtained by conducting the similar method to the above against the polyarylene comprising the repeating units (2) and (4).

An ion-exchange capacity of the polyarylene comprising the repeating unit (7) or the polyarylene consisting of the repeating unit (7), which is measured by titration method, is usually 0.5 to 6.5 meq/g.

Finally, a process for producing the dihalobiphenyl compound (1) will be illustrated.

The dihalobiphenyl compound (1) can be produced by reacting a compound represented by the formula (8):

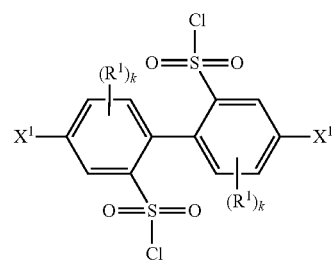

(8)

wherein R$^1$, X$^1$ and k are the same as the above (hereinafter, simply referred to as the compound (8)), with a compound represented by the formula (9):

A-H (9)

wherein A is the same as the above (hereinafter, simply referred to as the compound (9)) in the presence of a tertiary amine compound or a pyridine compound.

Examples of the compound (8) include 4,4'-dichlorobiphenyl-2,2'-disulfonyl dichloride, 4,4'-dibromobiphenyl-2,2'-disulfonyl dichloride, 3,3'-dimethyl-4,4'-dichlorobiphenyl-2,2'-disulfonyl dichloride, 5,5'-dimethyl-4,4'-dichlorobiphenyl-2,2'-disulfonyl dichloride, 6,6'-dimethyl-4,4'-dichlorobiphenyl-2,2'-disulfonyl dichloride, 3,3'-dimethoxy-4,4'-dichlorobiphenyl-2,2'-disulfonyl dichloride, 5,5'-dimethoxy-4,4'-dichlorobiphenyl-2,2'-disulfonyl dichloride, 6,6'-dimethoxy-4,4'-dichlorobiphenyl-2,2'-disulfonyl dichloride, 3,3'-diphenyl-4,4'-dichlorobiphenyl-2,2'-disulfonyl dichloride, 3,3'-diacetyl-4,4'-dichlorobiphenyl-2,2'-disulfonyl dichloride, 5,5'-diacetyl-4,4'-dichlorobiphenyl-2,2'-disulfonyl dichloride, and 6,6'-diacetyl-4,4'-dichlorobiphenyl-2,2'-disulfonyl dichloride, and 4,4'-dichlorobiphenyl-2,2'-disulfonyl dichloride and 4,4'-dibromobiphenyl-2,2'-disulfonyl dichloride are preferable. As the compound (8), a commercially available one may be used, and one produced according to known methods described, for example, in Bull. Soc. Chim. Fr., 4, 49 (1931), 1047-1049 or the like.

Examples of the compound (9) include isopropanol, isobutanol, 2,2-dimethylpropanol, cyclohexanol, n-octanol, n-pentadecanol, n-icosanol, diethylamine, diisopropylamine, 2,2- dimethylpropylamine, n-dodecylamine and n-icosylamine. As the compound (9), a commercially available one is usually used.

The amount of the compound (9) to be used is usually 0.2 mole or more per 1 mole of the group represented by —SO$_2$Cl in the compound (8) and there is no specific upper limit. When the compound (9) is a liquid at the reaction temperature, large excess thereof may be used also to serve as the reaction solvent. The practical amount of the compound (9) to be used is 0.5 to 2 moles per 1 mole of the group represented by —SO$_2$Cl in the compound (8).

Examples of the tertiary amine compound include trimethylamine, triethylamine, tri(n-propyl)amine, tri(n-butyl)amine, diisopropylethylamine, tri(n-octyl)amine, tri(n-decyl)amine, triphenylamine, N,N-dimethylaniline, N,N,N',N'-tetramethylethylenediamine and N-methylpyrrolidine. A commercially available tertiary amine compound is usually used. The amount of the tertiary amine compound to be used is usually 1 mole or more per 1 mole of the group represented by —SO$_2$Cl in the compound (8) and there is no specific upper limit. When the tertiary amine compound is a liquid at the reaction temperature, large excess thereof may be used also to serve as the reaction solvent. The practical amount of the tertiary amine compound to be used is 1 to 30 moles, preferably 0.5 to 20 moles and more preferably 1 to 10 moles per 1 mole of the group represented by —SO$_2$Cl in the compound (8).

Examples of the pyridine compound include pyridine and 4-dimethylaminopyridine. A commercially available pyridine compound is usually used. The amount of the pyridine compound to be used is usually 1 mole or more per 1 mole of the group represented by —SO$_2$Cl in the compound (8) and there is no specific upper limit. When the pyridine compound is a liquid at the reaction temperature, large excess thereof may be used also to serve as the reaction solvent. The practical amount of the pyridine compound to be used is 1 to 30 moles, preferably 1 to 20 moles and more preferably 1 to 10 moles per 1 mole of the group represented by —SO$_2$Cl in the compound (8).

The reaction of the compound (8) and the compound (9) is usually conducted by mixing the compound (8), the compound (9) and the tertiary amine compound or the pyridine compound in the presence of a solvent. The mixing order is not particularly limited.

Examples of the solvent include an aromatic hydrocarbon solvent such as toluene and xylene; an ether solvent such as diethyl ether, tetrahydrofuran and 1,4-dioxane; an aprotic polar solvent such as dimethylsulfoxide, N-methyl-2-pyrrolidone, N,N-dimethylformamide, N,N-dimethylacetamide and hexamethylphosphoric triamide; a halogenated hydrocarbon solvent such as dichloromethane, chloroform, dichloroethane, chlorobenzene and dichlorobenzene. Alternatively, as described above, when the compound (9), the tertiary amine compound or the pyridine compound is a liquid at the reaction temperature, they may be used as the reaction solvent. The solvent may be used alone and two or more kinds thereof may be mixed and used. The amount of the solvent is not particularly limited.

The temperature of the reaction of the compound (8) with the compound (9) is usually −30 to 150° C., and preferably −10 to 70° C. The reaction time is usually 0.5 to 24 hours.

After completion of the reaction, for example, an organic layer containing the dihalobiphenyl compound (1) can be obtained by adding water or an aqueous acid solution and if necessary, a water-insoluble organic solvent to the reaction mixture followed by extraction. The dihalobiphenyl compound (1) can be isolated by concentrating the organic layer obtained, if necessary, after washing with water or an aqueous alkali solution. The dihalobiphenyl compound (1) isolated may be further purified by a conventional means such as silica gel chromatography and recrystallization.

Examples of the water-insoluble organic solvent include an aromatic hydrocarbon solvent such as toluene and xylene; an aliphatic hydrocarbon solvent such as hexane and heptane; a halogenated hydrocarbon solvent such as dichloromethane, dichloroethane and chloroform; and an ester solvent such as ethyl acetate. The amount thereof is not particularly limited.

The dihalobiphenyl compound (1) can also be produced by reacting the compound (8) with a compound represented by the formula (10):

$$A\text{-}M \qquad (10)$$

wherein A is the same meaning as above and M represents an alkali metal atom (hereinafter, simply referred to as the compound (10)).

Examples of the alkali metal atom include lithium, sodium, potassium and cesium.

Examples of the compound (10) include lithium isopropoxide, lithium isobutoxide, lithium 2,2-dimethylpropoxide, lithium cyclohexyloxide, lithium diethylamide, lithium diisopropylamide, lithium 2,2-dimethylpropylamide, lithium n-dodecylamide, lithium n-icosylamide, sodium isobutoxide and potassium isobutoxide. As the compound (10), a commercially available one may be used and one produced according to known methods may be used.

The amount of the compound (10) to be used is usually 0.2 to 2 moles per 1 mole of the group represented by —SO$_2$Cl in the compound (8).

The reaction of the compound (8) with the compound (10) is usually conducted by mixing the compound (8) with the compound (10) in the presence of a solvent. The mixing order is not particularly limited.

Examples of the solvent include an aromatic hydrocarbon solvent such as toluene and xylene; an ether solvent such as diethyl ether, tetrahydrofuran and 1,4-dioxane; an aprotic polar solvent such as dimethylsulfoxide, N-methyl-2-pyrrolidone, N,N-dimethylformamide, N,N-dimethylacetamide and hexamethylphosphoric triamide; a halogenated hydrocarbon solvent such as dichloromethane, chloroform, dichloroethane, chlorobenzene and dichlorobenzene. The solvent may be used alone and two or more kinds thereof may be mixed and used. The amount of the solvent to be used is not particularly limited.

The temperature of the reaction of the compound (8) with the compound (10) is usually −30 to 150° C., and preferably −10 to 70° C. The reaction time is usually 0.5 to 24 hours.

After completion of the reaction, an organic layer containing the dihalobiphenyl compound (1) can be obtained by adding water and if necessary, a water-insoluble organic solvent to the reaction mixture followed by extraction. The dihalobiphenyl compound (1) can be isolated by concentrating the organic layer obtained, if necessary, after washing with water or an aqueous alkali solution. The dihalobiphenyl compound (1) isolated may be further purified by a conventional means such as silica gel chromatography and recrystallization.

Examples of the water-insoluble organic solvent include the same as described above.

EXAMPLES

The present invention will be further illustrated by Examples in detail below, but the present invention is not limited to these Examples. The polyarylenes obtained were analyzed with gel permeation chromatography (hereinafter, simply referred to as GPC) (the analytical conditions were as followings), and the weight-average molecular weight (Mw) and number-average molecular weight (Mn) were calculated based on the results thereof.

<Analytical Conditions>

Measuring apparatus: CTO-10A (manufactured by Shimadzu Corporation)
Column: TSK-GEL (manufactured by Tosoh Corporation)
Column temperature: 40° C.
Eluent: N,N-dimethylacetamide containing lithium bromide (concentration of lithium bromide: 10 mmol/dm$^3$)
Flow rate: 0.5 mL/min.
Detection wavelength: 300 nm Example 1

Twenty five point two grams of 2,2-dimethylpropanol was dissolved in 200 mL g of tetrahydrofuran. To this, 151.6 mL of a hexane solution of n-butyl lithium (1.57M) was added dropwise. After that, the resultant mixture was stirred at room temperature for 1 hour to prepare a solution containing lithium 2,2-dimethylisopropoxide. To a solution obtained by dissolving 40 g of 4,4'-dichlorobiphenyl-2,2'-disulfonyl dichloride in 300 mL of tetrahydrofuran, the prepared solution containing lithium 2,2-dimethylisopropoxide was added dropwise at 0° C. and then, the resultant mixture was stirred at room temperature for 1 hour to effect reaction. After concentrating the reaction mixture, 1000 mL of ethyl acetate and 1000 mL of 2 mol % hydrochloric acid were added to the residue to stir for 30 minutes. After leaving the mixture, an organic layer was separated. The organic layer separated was washed with 1000 mL of an aqueous saturated sodium chloride solution, and then the solvent was distilled away under reduced pressure. The concentrated residue was purified with silica gel chromatography (solvent: chloroform). The solvent was distilled away form the eluate obtained under reduced pressure. The residue was dissolved in 500 mL of toluene at 70° C. followed by cooling to room temperature. The solids precipitated were separated by filtration. The solids separated were dried to obtain 31.2 g of white solids of di(2,2-dimethylpropyl) 4,4'-dichlorobiphenyl-2,2'-disulfonate. Yield: 62.6%.

$^1$H-NMR (CDCl$_3$, δ (ppm)): 0.92 (s, 18H), 3.69-3.86 (c, 4H), 7.34-7.37 (c, 2H), 7.59-7.62 (c, 2H), 8.03-8.04 (c, 2H)
Mass spectrum (m/z): 451 (M-C5H$_{11}$)

Example 2

Di(2,2-dimethylpropyl) 4,4'-dibromobiphenyl-2,2'-disulfonate was obtained according to the same manner as that of Example 1, except that 4,4'-dibromobiphenyl-2,2'-disulfonyl dichloride was used in place of 4,4'-dichlorobiphenyl-2,2'-disulfonyl dichloride.

$^1$H-NMR (CDCl$_3$, δ (ppm)): 0.92 (s, 18H), 3.68-3.86 (c, 4H), 7.30 (c, 2H), 7.73-7.77 (c, 2H), 8.18 (c, 2H)
Mass spectrum (m/z): 541 (M-C5H$_{11}$)

Example 3

Diisopropyl 4,4'-dichlorobiphenyl-2,2'-disulfonate was obtained according to the same manner as that of Example 1, except that isopropanol was used in place of 2,2-dimethylpropanol.

$^1$H-NMR (CDCl$_3$, δ (ppm)): 1.22 (d, 3H), 1.35 (d, 3H), 4.80-4.95 (c, 2H), 7.32-7.36 (c, 2H), 7.55-7.65 (c, 2H), 8.05 (c, 2H)
Mass spectrum (m/z): 466 (M$^+$)

Example 4

Seventy two milliliters of dimethylsulfoxide and 2.33 g of anhydrous nickel chloride were mixed to adjust to an inner temperature of 60° C. To this, 3.09 g of 2,2'-bipyridine was added followed by stirring at the same temperature for 10 minutes to prepare a nickel-containing solution.

To the solution obtained by dissolving 9.42 g of di(2,2-dimethylpropyl) 4,4'-dichlorobiphenyl-2,2'-disulfonate and 3.60 g of SUMIKA EXCEL PES 5200P represented by the following formula:

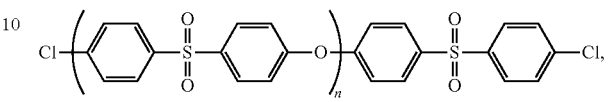

manufactured by Sumitomo Chemical Company, Limited, and Mw=94,000 and Mn=40,000 which were measured by the above analytical conditions, in 72 mL of dimethylsulfoxide, 3.30 g of powdery zinc was added and the mixture was adjusted at 60° C. The above-mentioned nickel-containing solution was poured therein and the polymerization reaction was conducted at 70° C. for 4 hours. The reaction mixture was added into 360 mL of methanol and then, 360 mL of 6 mol/L of hydrochloric acid was added thereto to stir for 1 hour. The solids precipitated were separated by filtration and dried to obtain 12.5 g of grayish white polyarylene comprising the repeating unit represented by the following:

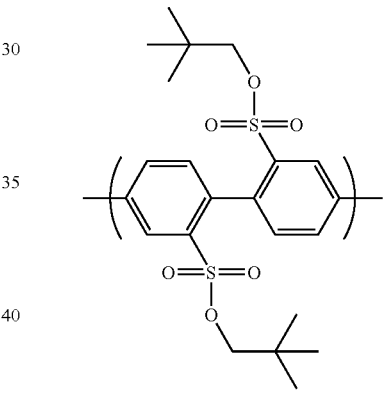

and the segment represented by the following:

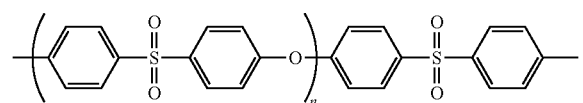

Mw=359,000, Mn=106,000.
$^1$H-NMR ((CD$_3$)$_2$SO$_2$, δ (ppm)): 0.86 (s), 3.70-3.90 (c), 7.21 (d), 7.93 (d), 7.00-8.50 (c)

Example 5

To the mixed solution of 91.5 g of tetrabutylammonium bromide and 160 mL of N-methyl-2-pyrrolidone, 10.7 g of the polyarylene obtained in Example 4 was added to effect reaction at 120° C. for 4 days. The reaction mixture was poured into 80 mL of 1.5 mol/L sulfuric acid to stir for 1 hour. The solids precipitated were separated by filtration. The solids separated were washed with methanol and then dried to obtain 5.7 g of the brown polyarylene comprising the repeating unit represented by the following:

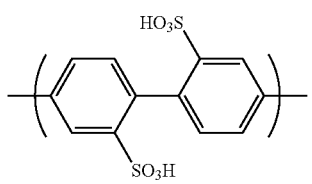

and the segment represented by the following:

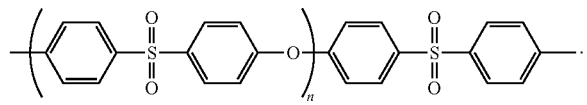

IR spectrum and $^1$H-NMR spectrum were measured to confirm that 2,2-dimethylpropoxysulfonyl groups were converted quantitatively to sulfonic acid groups. Mw of the polyarylene obtained was 593,000 and Mn thereof was 287,000. The ion-exchanged capacity was measured by the titration method to find 2.77 meq/g.

$^1$H-NMR ((CD$_3$)$_2$SO$_2$, δ (ppm)): 7.21 (d), 7.93 (d), 7.00-8.50 (c)

Example 6

Zero point eight milliliter of dimethylsulfoxide and 65 mg of anhydrous nickel chloride were mixed to adjust to an inner temperature of 60° C. To this, 86 mg of 2,2'-bipyridine was added followed by stirring at the same temperature for 10 minutes to prepare a nickel-containing solution.

To the solution obtained by dissolving 105 mg of di(2,2-dimethylpropyl) 4,4'-dichlorobiphenyl-2,2'-disulfonate in 0.8 mL of dimethylsulfoxide, 49 mg of powdery zinc was added and the mixture was adjusted at 60° C. The above-mentioned nickel-containing solution was poured therein and the polymerization reaction was conducted at 70° C. for 4 hours to obtain a reaction mixture containing the polyarylene consisting of the repeating unit represented by the following:

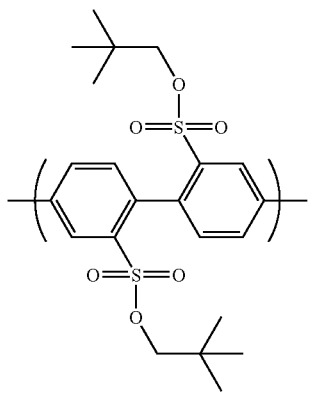

Mw of the polyarylene was 217,000, and Mn thereof was 49,000.

Example 7

Zero point eight milliliter of dimethylsulfoxide and 65 mg of anhydrous nickel chloride were mixed to adjust to an inner temperature of 60° C. To this, 86 mg of 2,2'-bipyridine was added followed by stirring at the same temperature for 10 minutes to prepare a nickel-containing solution.

To the solution obtained by dissolving 122 mg of di(2,2-dimethylpropyl) 4,4'-dibromobiphenyl-2,2'-disulfonate and 40 mg of SUMIKA EXCEL PES 5200P represented by the following formula:

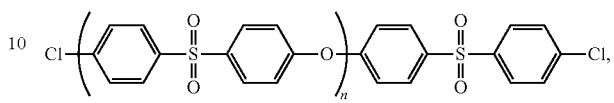

manufactured by Sumitomo Chemical Company, Limited, and Mw=94,000 and Mn=40,000 which were measured by the above analytical conditions, in 0.8 mL of dimethylsulfoxide, 49 mg of powdery zinc was added and the mixture was adjusted at 60° C. The above-mentioned nickel-containing solution was poured therein and the polymerization reaction was conducted at 70° C. for 4 hours to obtain a reaction mixture containing the polyarylene comprising the repeating unit represented by the following:

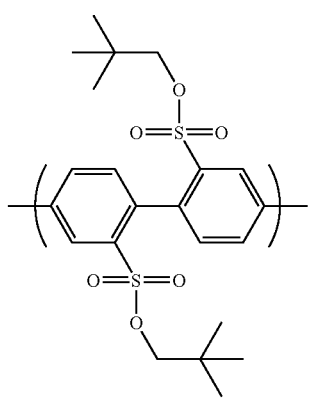

and the segment represented by the following:

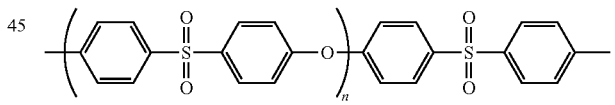

Mw of the polyarylene was 306,000, and Mn thereof was 65,000.

Example 8

Zero point eight milliliter of dimethylsulfoxide and 65 mg of anhydrous nickel chloride were mixed to adjust to an inner temperature of 60° C. To this, 86 mg of 2,2'-bipyridine was added followed by stirring at the same temperature for 10 minutes to prepare a nickel-containing solution.

To the solution obtained by dissolving 122 mg of di(2,2-dimethylpropyl) 4,4'-dibromobiphenyl-2,2'-disulfonate in 0.8 mL of dimethylsulfoxide, 49 mg of powdery zinc was added and the mixture was adjusted at 60° C. The above-mentioned nickel-containing solution was poured therein and the polymerization reaction was conducted at 70° C. for 4 hours to obtain a reaction mixture containing the polyarylene consisting of the repeating unit represented by the following:

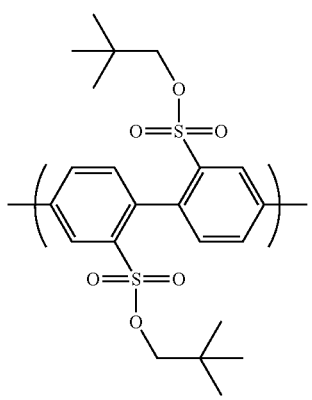

Mw of the polyarylene was 488,000, and Mn thereof was 63,000.

Example 9

To the reaction glass vessel equipped with a cooling apparatus, 42 mg of bis(octadiene)nickel (0), 26 mg of 2,2'-bipyridine, 100 mg of powdery zinc and 4 mL of N-methyl-2-pyrrolidone were added in an atmosphere of nitrogen to stir at 70° C. for 30 minutes. To this, the solution obtained by dissolving 400 mg of di(2,2-dimethylpropyl) 4,4'-dichlorobiphenyl-2,2'-disulfonate in 2 mL of N-methyl-2-pyrrolidone was added and the polymerization reaction was conducted at 70° C. for 4 hours to obtain the reaction mixture containing the polyarylene consisting of the repeating unit represented by the following:

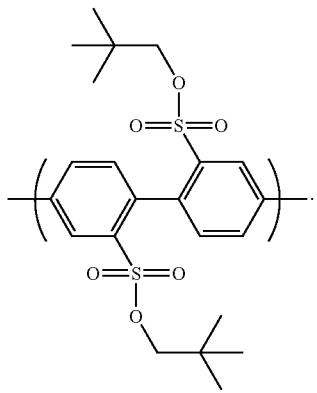

Mw of the polyarylene was 118,000 and Mn thereof was 41,000.

Example 10

To the reaction glass vessel equipped with a cooling apparatus, 42 mg of bis(octadiene)nickel (0), 26 mg of 2,2'-bipyridine, 100 mg of powdery zinc and 3 mL of N-methyl-2-pyrrolidone were added in an atmosphere of nitrogen to stir at 70° C. for 30 minutes. To this, the solution obtained by dissolving 400 mg of di(2,2-dimethylpropyl) 4,4'-dichlorobiphenyl-2,2'-disulfonate in 2 mL of N-methyl-2-pyrrolidone was added. Further, a solution obtained by dissolving 77 mg of SUMIKA EXCEL PES 5200P represented by the following formula:

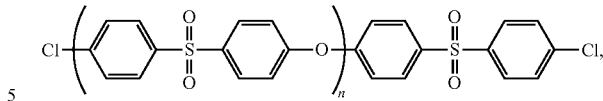

manufactured by Sumitomo Chemical Company, Limited, and Mw=94,000 and Mn=40,000 which were measured by the above analytical conditions, in 2 mL of N-methyl-2-pyrrolidone was added to the resultant mixture. The polymerization reaction was conducted at 70° C. for 4 hours to obtain the reaction mixture containing the polyarylene comprising the repeating unit represented by the following:

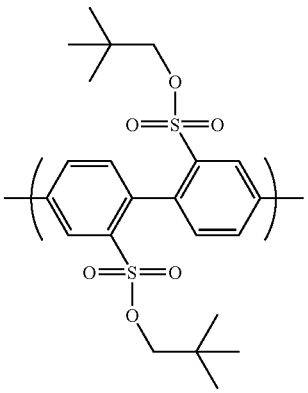

and the segment represented by the following:

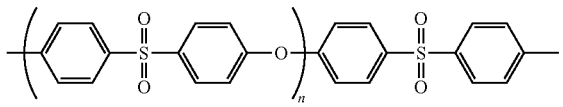

Mw of the polyarylene was 199,000, and Mn thereof was 63,000.

Example 11

To the reaction glass vessel equipped with a cooling apparatus, 17 mg of nickel bromide, 18 mg of 2,2'-bipyridine, 100 mg of powdery zinc and 3 mL of N,N-dimethylacetamide were added at room temperature in an atmosphere of nitrogen to prepare a nickel-containing solution. To this, the solution obtained by dissolving 400 mg of di(2,2-dimethylpropyl) 4,4'-dichlorobiphenyl-2,2'-disulfonate in 2 mL of N,N-dimethylacetamide was added and the polymerization reaction was conducted at 70° C. for 4 hours to obtain the reaction mixture containing the polyarylene consisting of the repeating unit represented by the following:

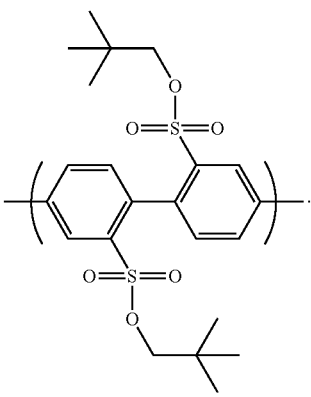

Mw of the polyarylene was 223,000 and Mn thereof was 76,000.

Example 12

To the reaction glass vessel equipped with a cooling apparatus, 141 mg of bis(octadiene)nickel (0), 88 mg of 2,2'-bipyridine, 84 mg of powdery zinc and 3 mL of N-methyl-2-pyrrolidone were added in an atmosphere of nitrogen to stir at 70° C. for 30 minutes. To this, the solution obtained by dissolving 300 mg of diisopropyl 4,4'-dichlorobiphenyl-2,2'-disulfonate in 1 mL of N-methyl-2-pyrrolidone was added and the polymerization reaction was conducted at 70° C. for 4 hours to obtain the reaction mixture containing the polyarylene consisting of the repeating unit represented by the following:

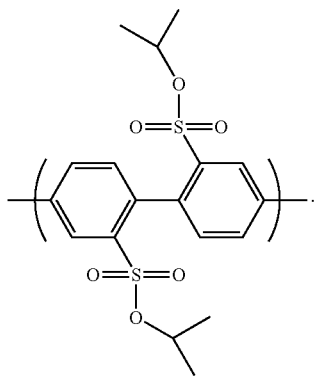

Mw of the polyarylene was 10,000 and Mn thereof was 8,000.

Example 13

To the reaction glass vessel equipped with a cooling apparatus, 42 mg of bis(octadiene)nickel (0), 26 mg of 2,2'-bipyridine, 100 mg of powdery zinc and 4 mL of N-methyl-2-pyrrolidone were added in an atmosphere of nitrogen to stir at 70° C. for 30 minutes to prepare a nickel-containing solution. To this, the solution obtained by dissolving 200 mg of di(2,2-dimethylpropyl) 4,4'-dichlorobiphenyl-2,2'-disulfonate and 56 mg of 1,4-dichlorobenzene in 2 mL of N-methyl-2-pyrrolidone was added. The polymerization reaction was conducted at 70° C. for 4 hours to obtain the reaction mixture containing the polyarylene comprising the repeating unit represented by the following:

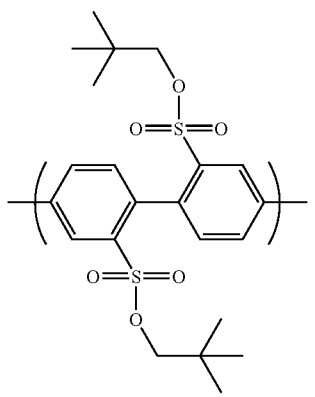

and the repeating unit represented by the following:

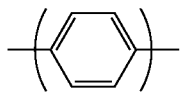

Mw of the polyarylene was 71,000, and Mn thereof was 24,000.

Example 14

To the reaction glass vessel equipped with a cooling apparatus, 42 mg of bis(octadiene)nickel (0), 26 mg of 2,2'-bipyridine, 100 mg of powdery zinc and 4 mL of N-methyl-2-pyrrolidone were added in an atmosphere of nitrogen to stir at 70° C. for 30 minutes to prepare a nickel-containing solution. To this, the solution obtained by dissolving 200 mg of di(2,2-dimethylpropyl) 4,4'-dichlorobiphenyl-2,2'-disulfonate and 131 mg of 2,5-dichloro-4'-phenoxybenzophenone in 2 mL of N-methyl-2-pyrrolidone was added. The polymerization reaction was conducted at 70° C. for 4 hours to obtain the reaction mixture containing the polyarylene comprising the repeating unit represented by the following:

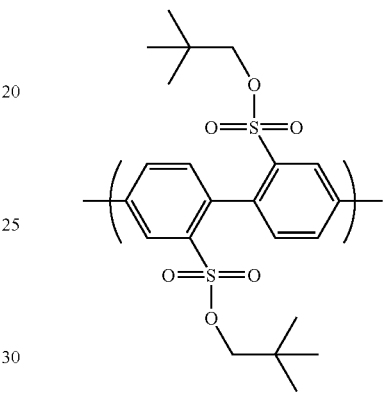

and the repeating unit represented by the following:

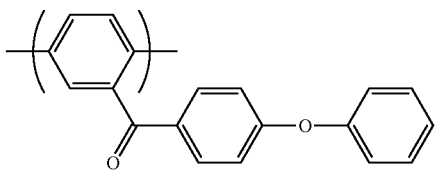

Mw of the polyarylene was 44,000, and Mn thereof was 20,000.

Example 15

The reaction mixture containing the polyarylene consisting of the repeating unit represented by the following

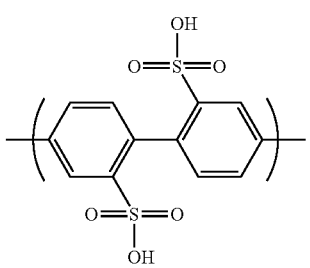

can be obtained by mixing the polyarylene obtained in Example 12 with an acid.

INDUSTRIAL APPLICABILITY

The dihalobiphenyl compound of the present invention is useful as a monomer of a polyarylene which can be easily converted to a polyarylene having sulfonic acid groups which is useful as a polyelectrolyte for proton-exchange membrane fuel cell.

The invention claimed is:

1. A polyarylene comprising a repeating unit represented by the formula (2):

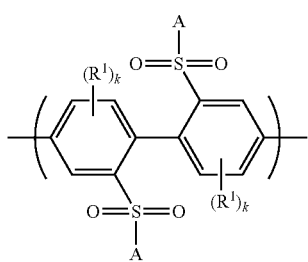

(2)

wherein

A represents a C1-C20 alkoxy group, and the above-mentioned alkoxy group may be substituted with at least one group selected from the group consisting of a fluorine atom, a C1-C20 alkoxy group, a C6-C20 aryl group, a C6-C20 aryloxy group, a C2-C20 acyl group and a cyano group, $R^1$ represents a fluorine atom, a C1-C20 alkyl group, a C1-C20 alkoxy group, a C6-C20 aryl group, a C6-C20 aryloxy group, a C2-C20 acyl group or a cyano group, and the C1-C20 alkyl group, the C1-C20 alkoxy group, the C6-C20 aryl group, the C6-C20 aryloxy group and the C2-C20 acyl group may be substituted with at least one substituent selected from the group consisting of a fluorine atom, a cyano group, a C1-C20 alkoxy group, a C6-C20 aryl group and a C6-C20 aryloxy group, and when multiple $R^1$s exist, $R^1$s may be the same groups or different groups, and the neighboring two $R^1$s may be bonded to form a ring, and k represents an integer of 0 to 3.

2. A polyarylene consisting of a repeating unit represented by the formula (2) according to claim 1.

3. The polyarylene according to claim 1, wherein the polyarylene comprises a repeating unit represented by the formula (2) according to claim 1 and a segment represented by the formula (3):

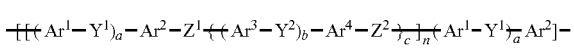

(3)

wherein a, b and c represent the same or different, and each represents 0 or 1, and n represents an integer of 5 or more, $Ar^1$, $Ar^2$, $Ar^3$ and $Ar^4$ are the same or different, and each represents a divalent aromatic group, and the divalent aromatic group may be substituted with at least one substituent selected from the group consisting of a C1-C20 alkyl group which may be substituted with at least one substituent selected from the group consisting of a fluorine atom, a cyano group, a C1-C20 alkoxy group, a C6-C20 aryl group and a C6-C20 aryloxy group;

a C1-C20 alkoxy group which may be substituted with at least one substituent selected from the group consisting of a fluorine atom, a cyano group, a C1-C20 alkoxy group, a C6-C20 aryl group and a C6-C20 aryloxy group;

a C6-C20 aryl group which may be substituted with at least one substituent selected from the group consisting of a fluorine atom, a cyano group, a C1-C20 alkoxy group and a C6-C20 aryloxy group;

a C6-C20 aryloxy group which may be substituted with at least one substituent selected from the group consisting of a fluorine atom, a cyano group, a C1-C20 alkoxy group and a C6-C20 aryloxy group; and a C2-C20 acyl group which may be substituted with at least one substituent selected from the group consisting of a fluorine atom, a cyano group, a C1-C20 alkoxy group, a C6-C20 aryl group and a C6-C20 aryloxy group, $Y^1$ and $Y^2$ are the same or different, and each represents a single bond, —CO—, —SO$_2$—, —C(CH$_3$)$_2$—, —C(CF$_3$)$_2$— or a fluorene-9,9-diyl group, and $Z^1$ and $Z^2$ are the same or different, and each represents —O— or —S—.

4. The polyarylene according to claim 1, wherein the polyarylene comprises a repeating unit represented by the formula (2) according to claim 1 and a repeating unit represented by the formula (4):

(4)

wherein $Ar^5$ represents a divalent aromatic group, and the divalent aromatic group may be substituted with at least one substituent selected from the group consisting of a C1-C20 alkyl group which may be substituted with at least one substituent selected from the group consisting of a fluorine atom, a cyano group, a C1-C20 alkoxy group, a C6-C20 aryl group and a C6-C20 aryloxy group;

a C1-C20 alkoxy group which may be substituted with at least one substituent selected from the group consisting of a fluorine atom, a cyano group, a C1-C20 alkoxy group, a C6-C20 aryl group and a C6-C20 aryloxy group;

a C6-C20 aryl group which may be substituted with at least one substituent selected from the group consisting of a fluorine atom, a cyano group, a C1-C20 alkoxy group and a C6-C20 aryloxy group;

a C6-C20 aryloxy group which may be substituted with at least one substituent selected from the group consisting of a fluorine atom, a cyano group, a C1-C20 alkoxy group and a C6-C20 aryloxy group; and a C2-C20 acyl group which may be substituted with at least one substituent selected from the group consisting of a fluorine atom, a cyano group, a C1-C20 alkoxy group, a C6-C20 aryl group and a C6-C20 aryloxy group.

5. A process for producing a polyarylene comprising the repeating unit represented by the formula (2):

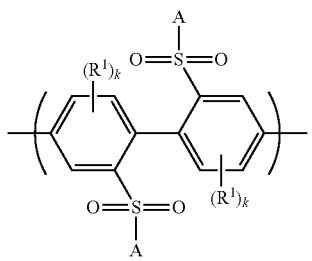

(2)

wherein A represents a C1-C20 alkoxy group, and the above-mentioned alkoxy group may be substituted with at least one group selected from the group consisting of a fluorine atom, a C1-C20 alkoxy group, a C6-C20 aryl group, a C6-C20 aryloxy group, a C2-C20 acyl group and a cyano group, $R^1$ represents a fluorine atom, a C1-C20 alkyl group, a C1-C20 alkoxy group, a C6-C20 aryl group, a C6-C20 aryloxy group, a C2-C20 acyl group or a cyano group, and the C1-C20 alkyl group, the C1-C20 alkoxy group, the C6-C20 aryl group, the C6-C20 aryloxy group and the C2-C20 acyl group may be substituted with at least one substituent selected from the group consisting of a fluorine atom, a cyano group, a C1-C20 alkoxy group, a C6-C20 aryl group and a C6-C20 aryloxy group, and when multiple $R^1$s exist, $R^1$s may be the same groups or different groups, and the neighboring two $R^1$s may be bonded to form a ring, and k represents an integer of 0 to 3, which comprises polymerizing a monomer composition comprising the dihalobiphenyl compound represented by formula (1) in the presence of a nickel compound:

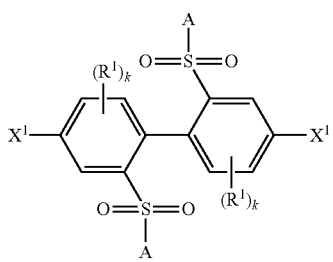

(1)

wherein A represents a C1-C20 alkoxy group, and the above-mentioned alkoxy group may be substituted with at least one group selected from the group consisting of a fluorine atom, a C1-C20 alkoxy group, a C6-C20 aryl group, a C6-C20 aryloxy group, a C2-C20 acyl group and a cyano group, $R^1$ represents a fluorine atom, a C1-C20 alkyl group, a C1-C20 alkoxy group, a C6-C20 aryl group, a C6-C20 aryloxy group, a C2-C20 acyl group or a cyano group, and the C1-C20 alkyl group, the C1-C20 alkoxy group, the C6-C20 aryl group, the C6-C20 aryloxy group and the C2-C20 acyl group may be substituted with at least one substituent selected from the group consisting of a fluorine atom, a cyano group, a C1-C20 alkoxy group, a C6-C20 aryl group and a C6-C20 aryloxy group, and when multiple $R^1$s exist, $R^1$s may be the same groups or different groups, and the neighboring two $R^1$s may be bonded to form a ring, $X^1$ represents a chlorine atom, a bromine atom or an iodine atom, and k represents an integer of 0 to 3.

6. The process for producing a polyarylene according to claim 5, wherein the monomer composition comprises the dihalobiphenyl compound represented by the formula (1):

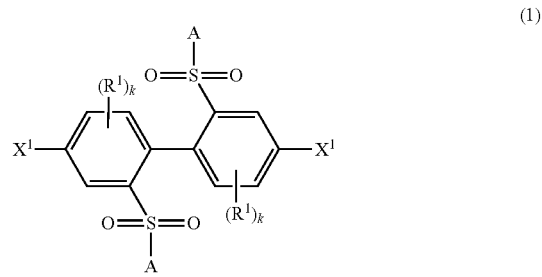

(1)

wherein A represents a C1-C20 alkoxy group, and the above-mentioned alkoxy group may be substituted with at least one group selected from the group consisting of a fluorine atom, a C1-C20 alkoxy group, a C6-C20 aryl group, a C6-C20 aryloxy group, a C2-C20 acyl group and a cyano group, $R^1$ represents a fluorine atom, a C1-C20 alkyl group, a C1-C20 alkoxy group, a C6-C20 aryl group, a C6-C20 aryloxy group, a C2-C20 acyl group or a cyano group, and the C1-C20 alkyl group, the C1-C20 alkoxy group, the C6-C20 aryl group, the C6-C20 aryloxy group and the C2-C20 acyl group may be substituted with at least one substituent selected from the group consisting of a fluorine atom, a cyano group, a C1-C20 alkoxy group, a C6-C20 aryl group and a C6-C20 aryloxy group, and when multiple $R^1$s exist, $R^1$s may be the same groups or different groups, and the neighboring two $R^1$s may be bonded to form a ring, $X^1$ represents a chlorine atom, a bromine atom or an iodine atom, and k represents an integer of 0 to 3, and a compound represented by the formula (5):

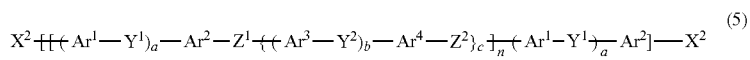

(5)

wherein a, b and c represent the same or different, and each represents 0 or 1, and n represents an integer of 5 or more, $Ar^1$, $Ar^2$, $Ar^3$ and $Ar^4$ are the same or different, and each represents a divalent aromatic group, and the divalent aromatic group may be substituted with at least one substituent selected from the group consisting of a C1-C20 alkyl group which may be substituted with at least one substituent selected from the group consisting of a fluorine atom, a cyano group, a C1-C20 alkoxy group, a C6-C20 aryl group and a C6-C20 aryloxy group;

a C1-C20 alkoxy group which may be substituted with at least one substituent selected from the group consisting of a fluorine atom, a cyano group, a C1-C20 alkoxy group, a C6-C20 aryl group and a C6-C20 aryloxy group;

a C6-C20 aryl group which may be substituted with at least one substituent selected from the group consisting of a fluorine atom, a cyano group, a C1-C20 alkoxy group and a C6-C20 aryloxy group;

a C6-C20 aryloxy group which may be substituted with at least one substituent selected from the group consisting of a fluorine atom, a cyano group, a C1-C20 alkoxy group and a C6-C20 aryloxy group; and a C2-C20 acyl group which may be substituted with at least one substituent selected from the group consisting of a fluorine atom, a cyano group, a C1-C20 alkoxy group, a C6-C20 aryl group and a C6-C20 aryloxy group, $Y^1$ and $Y^2$ are the same or different, and each represents a single bond, —CO—, —$SO_2$—, —$C(CH_3)_2$—, —$C(CF_3)_2$— or a fluorene-9,9-diyl group, and $Z^1$ and $Z^2$ are the same or different, and each represents —O— or —S—, and $X^2$ represents a chlorine atom, a bromine atom or an iodine atom.

7. The method for producing a polyarylene comprising the repeating unit represented by the formula (2):

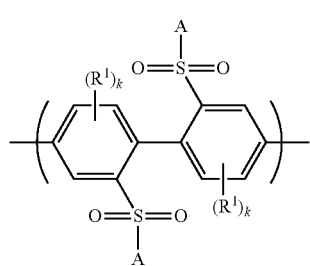

(2)

wherein A represents a C1-C20 alkoxy group, and the above-mentioned alkoxy group may be substituted with at least one group selected from the group consisting of a fluorine atom, a C1-C20 alkoxy group, a C6-C20 aryl group, a C6-C20 aryloxy group, a C2-C20 acyl group and a cyano group, $R^1$ represents a fluorine atom, a C1-C20 alkyl group, a C1-C20 alkoxy group, a C6-C20 aryl group, a C6-C20 aryloxy group, a C2-C20 acyl group or a cyano group, and the C1-C20 alkyl group, the C1-C20 alkoxy group, the C6-C20 aryl group, the C6-C20 aryloxy group and the C2-C20 acyl group may be substituted with at least one substituent selected from the group consisting of a fluorine atom, a cyano group, a C1-C20 alkoxy group, a C6-C20 aryl group and a C6-C20 aryloxy group, and when multiple $R^1$s exist, Ws may be the same groups or different groups, and the neighboring two $R^1$s may be bonded to form a ring, and k represents an integer of 0 to 3, which comprises polymerizing a monomer composition comprising the dihalobiphenyl compound represented by formula (1) in the presence of a nickel compound,

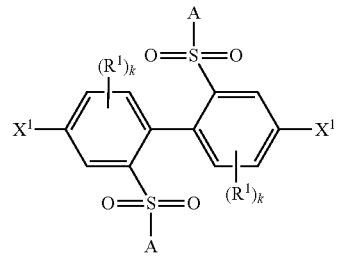

(1)

wherein A represents a C1-C20 alkoxy group, and the above-mentioned alkoxy group may be substituted with at least one group selected from the group consisting of a fluorine atom, a C1-C20 alkoxy group, a C6-C20 aryl group, a C6-C20 aryloxy group, a C2-C20 acyl group and a cyano group, $R^1$ represents a fluorine atom, a C1-C20 alkyl group, a C1-C20 alkoxy group, a C6-C20 aryl group, a C6-C20 aryloxy group, a C2-C20 acyl group or a cyano group, and the C1-C20 alkyl group, the C1-C20 alkoxy group, the C6-C20 aryl group, the C6-C20 aryloxy group and the C2-C20 acyl group may be substituted with at least one substituent selected from the group consisting of a fluorine atom, a cyano group, a C1-C20 alkoxy group, a C6-C20 aryl group and a C6-C20 aryloxy group, and when multiple $R^1$s exist, $R^1$s may be the same groups or different groups, and the neighboring two $R^1$s may be bonded to form a ring, $X^1$ represents a chlorine atom, a bromine atom or an iodine atom, and k represents an integer of 0 to 3 wherein the monomer composition comprises the dihalobiphenyl compound represented by the formula (1) and a compound represented by the formula (6):

$$X^3—Ar^5—X^3 \quad (6)$$

wherein $Ar^5$ represents a divalent aromatic group, and the divalent aromatic group may be substituted with at least one substituent selected from the group consisting of a C1-C20 alkyl group which may be substituted with at least one substituent selected from the group consisting of a fluorine atom, a cyano group, a C1-C20 alkoxy group, a C6-C20 aryl group and a C6-C20 aryloxy group;

a C1-C20 alkoxy group which may be substituted with at least one substituent selected from the group consisting of a fluorine atom, a cyano group, a C1-C20 alkoxy group, a C6-C20 aryl group and a C6-C20 aryloxy group;

a C6-C20 aryl group which may be substituted with at least one substituent selected from the group consisting of a fluorine atom, a cyano group, a C1-C20 alkoxy group and a C6-C20 aryloxy group;

a C6-C20 aryloxy group which may be substituted with at least one substituent selected from the group consisting of a fluorine atom, a cyano group, a C1-C20 alkoxy group and a C6-C20 aryloxy group; and a C2-C20 acyl group which may be substituted with at least one substituent selected from the group consisting of a fluorine atom, a cyano group, a C1-C20 alkoxy group, a C6-C20 aryl group and a C6-C20 aryloxy group, and $X^3$ represents a chlorine atom, a bromine atom or an iodine atom.

8. A process for producing a polyarylene consisting of the repeating unit represented by the formula (2):

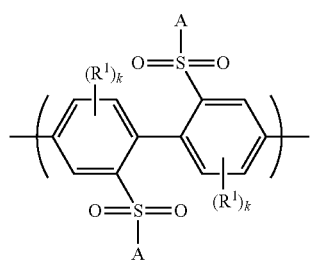

(2)

wherein A represents a C1-C20 alkoxy group, and the above-mentioned alkoxy group may be substituted with at least one group selected from the group consisting of a fluorine atom, a C1-C20 alkoxy group, a C6-C20 aryl group, a C6-C20 aryloxy group, a C2-C20 acyl group and a cyano group, $R^1$ represents a fluorine atom, a C1-C20 alkyl group, a C1-C20 alkoxy group, a C6-C20 aryl group, a C6-C20 aryloxy group, a C2-C20 acyl group or a cyano group, and the C1-C20 alkyl group, the C1-C20 alkoxy group, the C6-C20 aryl group, the C6-C20 aryloxy group and the C2-C20 acyl group may be substituted with at least one substituent selected from the group consisting of a fluorine atom, a cyano group, a C1-C20 alkoxy group, a C6-C20 aryl group and a C6-C20 aryloxy group, and when multiple $R^1$s exist, $R^1$s may be the same groups or different groups, and the neighboring two $R^1$s may be bonded to form a ring, and k represents an integer of 0 to 3, which comprises polymerizing the dihalobiphenyl compound represented by formula (1) only:

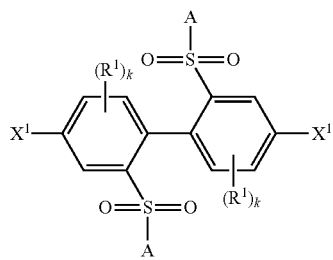

(1)

wherein A represents a C1-C20 alkoxy group, and the above-mentioned alkoxy group may be substituted with at least one group selected from the group consisting of a fluorine atom, a C1-C20 alkoxy group, a C6-C20 aryl group, a C6-C20 aryloxy group, a C2-C20 acyl group and a cyano group, $R^1$ represents a fluorine atom, a C1-C20 alkyl group, a C1-C20 alkoxy group, a C6-C20 aryl group, a C6-C20 aryloxy group, a C2-C20 acyl group or a cyano group, and the C1-C20 alkyl group, the C1-C20 alkoxy group, the C6-C20 aryl group, the C6-C20 aryloxy group and the C2-C20 acyl group may be substituted with at least one substituent selected from the group consisting of a fluorine atom, a cyano group, a C1-C20 alkoxy group, a C6-C20 aryl group and a C6-C20 aryloxy group, and when multiple $R^1$s exist, $R^1$s may be the same groups or different groups, and the neighboring two $R^1$s may be bonded to form a ring, $X^1$ represents a chlorine atom, a bromine atom or an iodine atom, and k represents an integer of 0 to 3.

9. The process for producing a polyarylene according to claim 5, wherein the nickel compound is bis(cyclooctadiene) nickel (0) and the polymerization is conducted in the presence of a nitrogen-containing bidentate ligand.

10. The process for producing a polyarylene according to claim 6, wherein the nickel compound is bis(cyclooctadiene) nickel (0) and the polymerization is conducted in the presence of a nitrogen-containing bidentate ligand.

11. The process for producing a polyarylene according to claim 7, wherein the nickel compound is bis(cyclooctadiene) nickel (0) and the polymerization is conducted in the presence of a nitrogen-containing bidentate ligand.

12. The process for producing a polyarylene according to claim 8, wherein the nickel compound is bis(cyclooctadiene) nickel (0) and the polymerization is conducted in the presence of a nitrogen-containing bidentate ligand.

13. The process for producing a polyarylene according to claim 5, wherein the nickel compound is bis(cyclooctadiene) nickel (0) and the polymerization is conducted in the presence of a nitrogen-containing bidentate ligand and zinc.

14. The process for producing a polyarylene according to claim 6, wherein the nickel compound is bis(cyclooctadiene) nickel (0) and the polymerization is conducted in the presence of a nitrogen-containing bidentate ligand and zinc.

15. The process for producing a polyarylene according to claim 7, wherein the nickel compound is bis(cyclooctadiene) nickel (0) and the polymerization is conducted in the presence of a nitrogen-containing bidentate ligand and zinc.

16. The process for producing a polyarylene according to claim 8, wherein the nickel compound is bis(cyclooctadiene) nickel (0) and the polymerization is conducted in the presence of a nitrogen-containing bidentate ligand and zinc.

17. The process for producing a polyarylene according to claim 5, wherein the nickel compound is a nickel halide and the polymerization is conducted in the presence of a nitrogen-containing bidentate ligand and zinc.

18. The process for producing a polyarylene according to claim 6, wherein the nickel compound is a nickel halide and the polymerization is conducted in the presence of a nitrogen-containing bidentate ligand and zinc.

19. The process for producing a polyarylene according to claim 7, wherein the nickel compound is a nickel halide and the polymerization is conducted in the presence of a nitrogen-containing bidentate ligand and zinc.

20. The process for producing a polyaryl ene according to claim 8, wherein the nickel compound is a nickel halide and the polymerization is conducted in the presence of a nitrogen-containing bidentate ligand and zinc.

21. The process for producing a polyarylene according to claim 5, wherein the used amount of the nickel compound is 0.01 to 5 moles per 1 mole of the monomer in the monomer composition.

22. The process for producing a polyaryl ene according to claim 6, wherein the used amount of the nickel compound is 0.01 to 5 moles per 1 mole of the monomer in the monomer composition.

23. The process for producing a polyarylene according to claim 7, wherein the used amount of the nickel compound is 0.01 to 5 moles per 1 mole of the monomer in the monomer composition.

24. The process for producing a polyarylene according to claim 8, wherein the used amount of the nickel compound is 0.01 to 5 moles per 1 mole of the monomer in the monomer composition.

25. The polyarylene according to claim 1, wherein the polyarylene contains the repeating unit represented by the formula (2) according to claim 1 and at least two repeating units represented by the formula (2) according to claim 1 are continued.

* * * * *